(12) United States Patent
Liu et al.

(10) Patent No.: US 10,521,905 B2
(45) Date of Patent: Dec. 31, 2019

(54) DIGITAL PATHOLOGICAL SLIDE SCANNING SYSTEM

(71) Applicant: NINGBO KONFOONG BIOINFORMATION TECH CO., LTD., Ningbo (CN)

(72) Inventors: Bingxian Liu, Ningbo (CN); Juyuan Xie, Ningbo (CN); Yanhui Wang, Ningbo (CN)

(73) Assignee: NINGBO KONFOONG BIOINFORMATION TECH CO., LTD., Ningbo (CN)

( * ) Notice: Subject to any disclaimer, the term of this patent is extended or adjusted under 35 U.S.C. 154(b) by 67 days.

(21) Appl. No.: 15/902,205

(22) Filed: Feb. 22, 2018

(65) Prior Publication Data
US 2019/0050980 A1 Feb. 14, 2019

(30) Foreign Application Priority Data

Aug. 11, 2017 (CN) .......................... 2017 1 0684440

(51) Int. Cl.
| | |
|---|---|
| G06T 7/00 | (2017.01) |
| H04L 9/08 | (2006.01) |
| H04L 9/32 | (2006.01) |
| G06T 5/00 | (2006.01) |
| G06K 9/00 | (2006.01) |

(Continued)

(52) U.S. Cl.
CPC ....... *G06T 7/0012* (2013.01); *G01N 21/6458* (2013.01); *G01N 21/6486* (2013.01); *G06K 9/00134* (2013.01); *G06K 9/4647* (2013.01); *G06T 5/009* (2013.01); *G06T 11/60* (2013.01); *G16H 30/20* (2018.01); *H04L 9/0838* (2013.01); *H04L 9/32* (2013.01); *G06T 2207/10056* (2013.01); *G06T 2207/20208* (2013.01); *G06T 2207/30024* (2013.01); *G06T 2207/30168* (2013.01); *G06T 2210/22* (2013.01); *G06T 2210/41* (2013.01)

(58) Field of Classification Search
None
See application file for complete search history.

(56) References Cited

U.S. PATENT DOCUMENTS

2013/0004037 A1\* 1/2013 Scheuering .......... A61B 6/5294
382/128

\* cited by examiner

*Primary Examiner* — Matthew C Bella
*Assistant Examiner* — Brian D Shin
(74) *Attorney, Agent, or Firm* — Terry M. Sanks, Esq.; Beusse Wolter Sanks & Maire, PLLC

(57) ABSTRACT

The present invention discloses a digital pathological section scanning system and relates to the field of a section scanning technology. The system comprises a scanning end, an image processing end, a remote server, a first client end and a second client end; wherein the scanning end scans a pathological section to form an original pathological section image and transmits the original pathological section image to the image processing end for processing; the image processing end processes the original pathological section image to form a digital pathological section image and sends the digital pathological section image to the remote server; the first client end transmits medical record information including attending physician information to the remote server; the remote server associates the digital pathologic section image with the attending physician information and saves the digital pathological section image in the storage unit corresponding to the attending physician information.

28 Claims, 16 Drawing Sheets

(51) Int. Cl.
    *G16H 30/20*     (2018.01)
    *G01N 21/64*     (2006.01)
    *G06K 9/46*     (2006.01)
    *G06T 11/60*     (2006.01)

T1'

T2

DIGITAL PATHOLOGICAL SLIDE SCANNING SYSTEM

CROSS-REFERENCE TO RELATED APPLICATIONS

The present application claims priority to and the benefit of Chinese Patent Application No. CN201710684440.7, filed on Aug. 11, 2017, the entire content of which is incorporated herein by reference.

BACKGROUND OF THE INVENTION

Field of the Invention

The present invention relates to the field of a section scanning technology, and more particularly, to a digital pathological section scanning system.

Description of the Related Art

It is one of the important examination methods to determine if any lesion and abnormity is found in corresponding tissues and organs of human body by observing a section tissue of human body, and such an examination method is usual in the modern medicine. Traditional way of observing a section is carried out by observing the section tissue on a slide through a microscope with a naked eye, which is labor intensive, and the observation result is not very accurate.

With the development of science and technology, there appears a digital section scanning system to replace the traditional section tissue observation. The digital section scanning system is a digital scanning system capable of scanning section tissue and forming the image of a cell on the surface of the section tissue. An image of the pathological section scanned by the digital section scanning system is not a normal image but an image that can be provided to a user for any zoom-in or zoom-out operation. When enlarging a local region of the image, the user can observe an enlarged view of the cell in this region, and therefore a physician can judge if any lesion and abnormity is found in corresponding tissues and organs of human body by observing the section tissue in a more clearly and accurate way.

However, the existing digital section scanning system typically generates a digital image of the pathological section only according to a scanning result without performing any further processing to the generated image. In addition, since the image bears rich and complex information, issues listed as follows occur, that is, the image will be partially unclear, the brightness will be uneven and other problems having an influence on the observation of the image will emerge, leading to the result that the physician cannot accurately observe details of the cell tissue somewhere in the image, affecting the final judgment.

SUMMARY OF THE INVENTION

Given that the foregoing problems exist in the prior art, the present invention provides a digital pathological section scanning system capable of improving the definition and readability of a digital pathological section, and eliminating unqualified digital pathological section images, thus increasing the efficiency for the physician to look for and read the digital pathological section.

The detailed technical schemes are as follows:

a digital pathological section scanning system, comprising: a scanning end, an image processing end, a remote server, a first client end and a second client end, wherein the scanning end is connected to the image processing end, and the remote server is connected to the image processing end, the first client end and the second client end, respectively;

wherein, the scanning end is used for scanning a pathological section to be scanned to form an original pathological section image, and for transmitting the original pathological section image to the image processing end for processing;

the image processing end is used for processing the original pathological section image transmitted by the scanning end to form a corresponding digital pathological section image and save the corresponding digital pathological section image, and for sending the digital pathological section image to the remote server;

wherein, the image processing end further comprises:

a first detection unit, for detecting a brightness value of the original pathological section image, and outputting a first detection result indicating whether the brightness value of the original pathological section image is qualified;

a second detection unit, for detecting the definition at the jointing region of the original pathological section image formed by jointing a plurality of digital pathological section images, and for outputting a second detection result indicating whether the definition at the jointing region is qualified;

an output unit, connected to the first detection unit and the second detection unit respectively, used for upon the first detection result and the second detection result, taking the original pathological section image having qualified brightness value and definition as the digital pathological section image, and sending the digital pathological section image to the remote server;

wherein, the first client end is used for transmitting a medical record information to the remote server, and the medical record information comprises an attending physician information representing an account of the attending physician which is selected by the first client end;

the remote server comprises a storage space having a storage unit corresponding to the information of each of the attending physician;

the remote server associates the obtained digital pathologic section image with the attending physician information included in the medical record information, and saves the digital pathological section image in the storage unit corresponding to the attending physician information;

the remote server simultaneously allows the second client end that has verified login to the attending physician account to access the digital pathological section saved in the storage unit corresponding to the attending physician account.

Preferably, the digital pathological section scanning system, wherein the first detection unit specifically comprises:

a first detection module, for detecting a brightness value of the original pathological section image;

a first standard module, providing a preset brightness range of a standard image corresponding to the original pathological section image;

a first comparison module, connected to the first detection module and the first standard module, respectively, for comparing the brightness value of the original pathological section image with the brightness range of the standard image;

outputting the first detection result indicating that the brightness value of the original pathological section image is qualified when the brightness value of the original pathological section image is within the brightness range of the standard image, and outputting the first detection result indicating that the brightness value of the original pathological section image is unqualified when the brightness value of the original pathological section image falls outside the brightness range of the standard image, Preferably, the digital pathological section scanning system, wherein the first detection unit further comprises:

an image compensation module, connected to the first comparison module, wherein, when the first comparison module outputs the first detection result indicating the brightness value of the original pathological section image is unqualified, the image compensation module outputs an illumination compensation instruction based on a difference between the brightness value of the unqualified original pathological section image and the brightness range of the standard image, then the image processing end feeds back the illumination compensation instruction to the scanning end to obtain the original pathological section image by controlling the scanning end to rescan.

Preferably, the digital pathological section scanning system, wherein the second detection unit specifically comprises:

a second detection module, processing the two digital pathological images that are jointed to each other, to obtain an image gradient of one digital pathological image to serve as a first gradient value, and to obtain an image gradient of the other digital pathological image to serve as a second gradient value;

a second standard module, providing a preset gradient ratio in advance;

a second comparison module, connected to the second detection module and the second standard module, respectively, for comparing the ratio of the first gradient value to the second gradient value with the preset gradient ratio, and when the ratio is not matched with the preset gradient ratio, it is determined that the definition of the jointing region where the two digital pathological images are jointed to each other is unqualified, and thus outputting the second detection result indicating the definition of the jointing region where the original pathological images are jointed to each other is unqualified.

Preferably, the digital pathological section scanning system, wherein when the first gradient value is less than or equal to the second gradient value, the preset gradient ratio is less than or equal to 1;

then the second comparison module compares the ratio of the first gradient value to the second gradient value with the preset gradient ratio, and according to the comparison result, when the ratio of the first gradient value to the second gradient value is less than the preset gradient ratio, it is determined that the definition of the jointing region where the two digital pathological images are jointed to each other is unqualified;

when the ratio of the first gradient value to the second gradient value is greater than or equal to the preset gradient ratio, it is determined that the definition of the jointing region where the two digital pathological images are jointed to each other is qualified.

Preferably, the digital pathological section scanning system, wherein when the first gradient value is greater than the second gradient value, the preset gradient ratio is greater than 1;

then the second comparison module compares the ratio of the first gradient value to the second gradient value with the preset gradient ratio, and according to the comparison result, when the ratio of the first gradient value to the second gradient value is greater than the preset gradient ratio, it is determined that the definition of the jointing region where the two digital pathological images are jointed to each other is unqualified;

when the ratio of the first gradient value to the second gradient value is less than the preset gradient ratio, it is determined that the definition of the jointing region where the two digital pathological images are jointed to each other is qualified.

Preferably, the digital pathological section scanning system, wherein the second detection unit further comprises:

an identification module, connected to the second comparison module, for identifying the jointing region on the digital pathological image where the second comparison module determines the definition of the digital pathological image is unqualified.

Preferably, the digital pathological section scanning system, wherein the second detection unit further comprises:

a storage module, connected to the second comparison module, for temporarily storing the digital pathological image whose definition is determined to be qualified by the second comparison module.

Preferably, the digital pathological section scanning system, wherein in the digital pathological section scanning system, section-cutting is performed on the human tissue of the same person, and two different original pathological section images are formed by scanning via the scanning end;

in the image processing end, the scanning system respectively detects the brightness value and the definition of the jointing region of the two original pathological section images, and forms two digital pathological section images respectively corresponding to the two original pathological section images, serving as a first section image and a second section image;

wherein, the first section image is located in a first XOY coordinate axis which functions one endpoint of the first section image as an original point, and the second section image is located in a second XOY coordinate axis which functions one endpoint of the second section image as an original point;

the image processing end further comprises:

an adjusting unit, connected to the output unit, for adjusting, before the digital pathological section image is sent out by the output unit, the second section image according to the relative position between the first section image and the second section image, and integrating the second section image and the first section image into a corresponding digital pathological section image to be sent to the remote server by the output unit.

Preferably, the digital pathological section scanning system, wherein the adjusting unit specifically comprises:

a background processing module, for expanding the outline size of the first section image, and filling the enlarged portion of the first section image with a blank background;

a first rotating module, connected to the background processing module, for aligning the endpoint in the second section image, coinciding with the original point of the second XOY coordinate axis, with a preset rotating point in the first section image;

a first grayscale processing module, connected to the first rotating module, for processing the first section image to obtain a gray value of a preset first determination point, and processing the second section image to obtain a gray value of a second determination point corresponding to the first determination point, followed by obtaining a grayscale comparison value under the current relative position between the first section image and the second section image;

a second rotating module, connected to the first rotating module, for rotating the second section image clockwise about the endpoint coinciding with the original point of the second XOY coordinate axis by a preset angle;

a determination module, connected to the first grayscale processing module and the second rotating module respectively, for determining, after the second rotating module rotates the second section image, whether the second section image has rotated about 360 degrees relative to an initial position, and outputting a determination result;

wherein, the first grayscale processing module is further configured to perform, according to the determination result, the grayscale processing again when the second section image has not rotated about 360 degrees relative to the initial position;

and the second rotating module is further configured to continue rotating, according to the determination result, the second section image when the second section image has not rotated about 360 degrees relative to the initial position;

an adjusting module, connected to the first grayscale processing module and the determination module, respectively, for obtaining, according to the determination result, the gray value with the smallest value when the second section image has rotated about 360 degrees relative to the initial position, and adjusting the second section image according to the relative position between the first section image and the second section image corresponding to the obtained grayscale value.

Preferably, the digital pathological section scanning system, wherein the background processing module enlarges the first section image to an image with a width and a height of A, and fills the enlarged portion of the first section image with a blank background;

wherein, $$A = \sqrt[2]{W_1^2 + H_1^2}$$

$W_1$ represents the width of the first section image;
$H_1$ represents the height of the first section image.

Preferably, the digital pathological section scanning system, wherein the value range of the coordinate (m, n) of the preset rotating point satisfies the follows:

$$0 \le m < W1 - W2;$$

$$0 \le n < H1 - H2;$$

wherein, m represents the X-axis coordinate of the preset rotating point in the first XOY coordinate axis;

n represents the Y-axis coordinate of the preset rotating point in the first XOY coordinate axis;

$W_1$ represents the width of the first section image;
$H_1$ represents the height of the first section image;
$W_2$ represents the width of the second section image;
$H_2$ represents the height of the second section image.

Preferably, the digital pathological section scanning system, wherein the preset coordinate of the first determination point has a preset value range;

then the first grayscale processing module further comprises:

a first grayscale processing component, for processing the first section image to obtain a gray value of each of the first determination point within the value range to serve as a first grayscale value;

a second grayscale processing component, for processing the second section image to obtain a gray value of each of the second determination point corresponding to each of the first determination point within the value range to serve as a second grayscale value;

a third grayscale processing component, connected to the first grayscale processing component and the second grayscale processing component, respectively, for obtaining, according to the first gray value and the corresponding second grayscale value, each corresponding grayscale comparison value respectively;

a grayscale acquisition component, connected to the third grayscale processing component, for obtaining the grayscale comparison value with the smallest value, serving as the grayscale comparison value under the current relative position between the first section image and the second section image.

Preferably, the digital pathological section scanning system, wherein the third grayscale processing component obtains the grayscale comparison value according to the following formula:

$$S(m,n) = \Sigma_{i=0,j=0}^{i=W_2-1, j=H_2-1} |P_1 - P_2|$$

wherein,

S(m,n) represents the grayscale comparison value;

(m,n) represent the coordinate value of the preset rotating point, m is the X-axis coordinate of the preset rotating point in the first XOY coordinate axis, n is the Y-axis coordinate of the preset rotating point in the first XOY coordinate axis;

(i, j) represent the coordinate value of the second determination point, i is the X-axis coordinate of the second determination point in the second XOY coordinate axis, j is the Y-axis coordinate of the second determination point in the second XOY coordinate axis;

$W_2$ represents the width of the second section image;
$H_2$ represents the height of the second section image.
$P_1$ represents the first grayscale value;
$P_2$ represents the second grayscale value.

Preferably, the digital pathological section scanning system, wherein the grayscale acquisition component obtains the grayscale comparison value with the smallest value, serving as the grayscale comparison value under the current relative position between the first section image and the second section image, and for recording the rotation angle of the second section image relative to the initial position;

the adjusting module rotates the second section image according to the rotation angle corresponding to the obtained grayscale comparison value with the smallest value.

Preferably, the digital pathological section scanning system, wherein a preview of the pathological section is obtained by pre-scanning before the scanning end scans the pathological section;

the image processing end further comprises:

an identification unit, for recognizing the preview to obtain a section tissue image in the preview;

the image processing end transmits the section tissue image back to the scanning end, and the scanning end scans the pathological section according to the section tissue image.

Preferably, the digital pathological section scanning system, wherein a blank section image is obtained by scanning via the scanning end in advance;

the identification unit specifically comprises:

an image acquisition module, obtaining a background image of the blank section image and the preview, respectively;

a second grayscale processing module, connected to the image acquisition module, for subtracting the gray value of the background image from the gray value of the preview to obtain a section information graph;

a first elimination module, connected to the second grayscale processing module, for performing traversal processing on the connected domains of the section information graph, and eliminating stains in the section information graph;

a second elimination module, connected to the first elimination module, for respectively judging, according to the attribute of the connected domain, whether each connected domain in the section information graph having been eliminated the stains is a section tissue, and eliminating the connected domain which is not the section tissue;

a retention module, connected to the second elimination module, for retaining the section information graph as the section tissue image after the connected domain which does not belong to the section tissue is eliminated, Preferably, the digital pathological section scanning system, wherein the image acquisition module comprises:

an acquiring component, for acquiring a background image of the blank section image and the preview respectively;

a clipping component, connected to the acquiring component, for cutting off the edge portions of the background image and the preview respectively.

Preferably, the digital pathological section scanning system, wherein the output unit specifically comprises:

a cutting module, for cutting the digital pathological section image into a plurality of local images;

a coordinate encryption module, connected to the cutting module, for respectively performing an encryption operation on the coordinate information of each of the local images to obtain an encrypted information of each of the local images;

wherein, the output unit sends the local images and the corresponding encrypted information to the remote server, so as to send the digital pathological section image to the remote server;

wherein, after the second client end accesses the remote server and obtains the stored local images and the corresponding encryption information associated to the digital pathological section image, each of the encrypted information is parsed to obtain the corresponding coordinate information, and according to the coordinate information, the local images are jointed in sequence to form a completed digital pathological section image and the completed digital pathological section image is displayed, so that a user of the second client end diagnoses the digital pathological section image.

Preferably, the digital pathological section scanning system, wherein the digital pathological section scanning system comprises a plurality of scanning ends, each of the scanning ends corresponding to one of the image processing ends;

each of the image processing ends has a unique authorization code, and each of the scanning ends has a unique machine code, and the authorization code and the machine code form a key;

the key is provided to the output unit of the image processing end for performing an encryption operation on the digital pathological section image, and the image processing end provides the key to the remote server while sending the digital pathological section image to the remote server.

Preferably, the digital pathological section scanning system, wherein each of the storage units in the remote server specifically comprises:

a first storage module, for storing the local images in the digital pathological section image;

a second storage module, for storing the encrypted information corresponding to each of the local images;

a third storage module, for storing the key corresponding to the digital pathological section image;

wherein, the remote server further comprises:

an access unit, connected to the storage space, for obtaining, upon the access request of the second client end, the local images, the encryption information and the key from the storage unit, and the obtained local images, the encryption information and the key are sent to the second client end.

Preferably, the digital pathological section scanning system, wherein the remote server specifically comprises:

a first acquiring unit, for acquiring the digital pathological section image sent by the image processing end;

a second acquiring unit, for acquiring the medical record information sent by the first client end;

a data analysis unit, connected to the second acquiring unit, for acquiring the attending physician information by analyzing the medical record information;

a distribution processing unit, connected to the data analysis unit, the first acquiring unit, the second acquiring unit and the storage space, respectively, for storing, according to the analyzed attending physician information, the corresponding medical record information and the digital pathological section image in the corresponding storage unit in the storage space, and in the storage unit, the digital pathological section image and the medical record information are saved in association with each another;

an authority authentication unit, connected to the storage space, for verifying the account information and the password of the attending physician account provided by the second client end;

and authorizing the second client end permission to access the medical record information and the digital pathological section image in the corresponding storage unit after the verification is passed; and a medical record processing unit, connected to the storage space, for diagnosing the digital pathological section image by the second client end by remote login to form a diagnostic report corresponding to the digital pathological section image, and the diagnostic report is saved in the storage unit in the storage space corresponding to the digital pathological section image.

Preferably, the digital pathological section scanning system, wherein the remote server further comprises:

a diagnosis prompt unit, connected to the medical record processing unit, for forming a diagnostic prompt information corresponding to the medical record information according to the generated diagnostic report; and a pushing unit, connected to the diagnosis prompt unit, for sending the diagnosis prompt information to the first client end outputting the medical record information.

Preferably, the digital pathological section scanning system, further comprising, a short message notification server, wherein the short message notification server provides an interface for connecting to the remote server, and the short message notification server further remotely connects to the second client end;

the remote server further comprises:

a notification unit, connected to the data analysis unit, for generating corresponding consultation prompt information according to the analyzed attending physician information;

wherein, calling the interface via the remote server to control the short message notification server to send the consultation prompt information to the second client end corresponding to the attending physician information.

Preferably, the digital pathological section scanning system, wherein the scanning end further comprises:

a section platform on which the pathological section to be scanned is placed for scanning by the scanning end;

an automatic loading device, disposed below the section platform and connected to the section platform, a plurality of the pathological sections to be scanned being placed in the automatic loading device, and the automatic loading device lifts a pathological section to be scanned to the section platform at a time, for scanning by the scanning end; and an illumination scanning device, disposed above the section platform, for scanning the pathological sections to be scanned placed on the section platform, to obtain the original pathological section image.

Preferably, the digital pathological section scanning system, wherein the illumination scanning device further comprises:

a LED light source, for providing a light source required for scanning when the scanning end scans the pathological section to be scanned;

a scanning unit, disposed at a side of the LED light source, for scanning the pathological section to be scanned; and a bright-to-fluorescence switching device, disposed on the scanning unit and connected to the scanning unit, for controlling the scanning unit to switch between a bright field scanning mode and a fluorescence scanning mode.

Preferably, the digital pathological section scanning system, wherein the automatic loading device comprises a section box and a loader;

wherein, a plurality of slides comprising the pathological sections to be scanned are placed in the section box in advance, and each of the slides has a preset number;

when the user selects the slide to be scanned according to the number, the loader pushes out the selected slide in the section box and places it in the section box of the section platform to be scanned by the illumination scanning device.

The beneficial effects of the above technical schemes are as follows: providing a digital pathological section scanning system, which can improve the definition and readability of the digital pathological section, and eliminate unqualified digital pathological section images, thus improving physician's reading efficiency.

BRIEF DESCRIPTION OF THE DRAWINGS

The accompanying drawings, together with the specification, illustrate exemplary embodiments of the present disclosure, and, together with the description, serve to explain the principles of the present invention.

DETAILED DESCRIPTION

Figure 1:
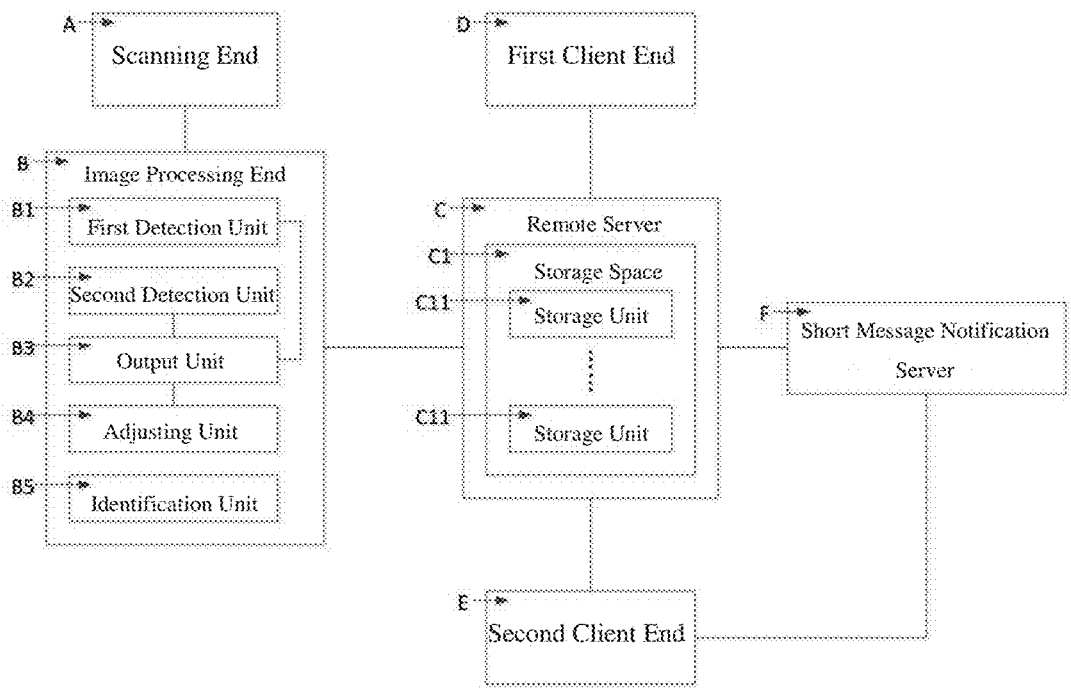
FIG. 1 is a schematic diagram of the overall structure of a digital pathological section scanning system in a preferred embodiment of the present invention.

The present disclosure will now be described more fully hereinafter with reference to the accompanying drawings, in which exemplary embodiments of the disclosure are shown. This disclosure may, however, be embodied in many different forms and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the term "plurality" means a number greater than one.

Hereinafter, certain exemplary embodiments according to the present disclosure will be described with reference to the accompanying drawings.

Given that the foregoing problems exist in the prior art, the present invention provides a digital pathological section scanning system, as shown in FIG. 1, comprising a scanning end A, an image processing end B, a remote server C, a first client end D and a second client end E, wherein the scanning end A is connected to the image processing end B, and the remote server C is connected to the image processing end B, the first client end D and the second client end E, respectively;

wherein, the scanning end A is used for scanning a pathological section to be scanned to form an original pathological section image, and for transmitting the original pathological section image to the image processing end for processing;

the image processing end B is used for processing the original pathological section image transmitted by the scanning end A to form a corresponding digital pathological section image and save the corresponding digital pathological section image, and for sending the digital pathological section image to the remote server C;

wherein, the image processing end B further comprises:

a first detection unit B1, for detecting a brightness value of the original pathological section image, and outputting a first detection result indicating whether the brightness value of the original pathological section image is qualified;

a second detection unit B2, for detecting the definition at the jointing region of the original pathological section image formed by jointing a plurality of digital pathological section images, and for outputting a second detection result indicating whether the definition at the jointing region is qualified;

an output unit B3, connected to the first detection unit B1 and the second detection unit B2 respectively, used for upon the first detection result and the second detection result, taking the original pathological section image having qualified brightness value and definition as the digital pathological section image, and sending the digital pathological section image to the remote server;

wherein, the first client end D is used for transmitting a medical record information to the remote server C, and the medical record information comprises an attending physician information representing an account of the attending physician which is selected by the first client end;

the remote server C comprises a storage space C1 having a storage unit C11 corresponding to the information of each of the attending physician;

the remote server C associates the obtained digital pathologic section image with the attending physician information included in the medical record information, and saves the digital pathological section image in the storage unit C11 corresponding to the attending physician information;

the remote server C simultaneously allows the second client end E, that has verified login to the attending physician account, to access the digital pathological section saved in the storage unit C11 corresponding to the attending physician account.

Specifically, in this embodiment, the above-mentioned scanning end A, i.e., a digital pathological section scanner, scans a pathological section on the scanner and forms an original pathological section image. It is necessary to set up an image processing end B to perform pre-processing on the original pathological section image prior to transmitting the image to the remote server C, such that the digital pathological section image obtained by scanning in the scanning end A is more clear and easy to identify. The image processing end B could be an image processing server.

Further, since most of the detections are carried out indoors, the image taken or detected by a medical device will be affected by indoor lighting, thus, a dark image is generated. In addition, it is through manpower to judge the brightness of the generated image. Only when person in charge judges that the brightness of the generated image is qualified can the image be sent to and be saved in the remote server C to be checked by the physician. However, such way of determination of the brightness is quite labor-intensive, moreover, it is too subjective with different kinds of criterions in mind, and the accuracy of determination thus cannot be guaranteed. The image transmitted to the remote server C still has certain problem in terms of brightness. In this embodiment, a first detection unit B1 is provided on the image processing end B for detecting the brightness value of the original pathological section image, and if the brightness values of some original pathological section images are unqualified, these original pathological section images determined to be unqualified will not be sent to the remote server C. The first detection unit B1 can be formed of a first processor in the image processing end B, that is, the first processor is adopted to determine the brightness of the original pathological section image.

In the meantime, since the original pathological section image is a very large image, in order to ensure the richness and integrity of the section tissue in the image to be displayed fully, it can be contemplated that a plurality of digital pathological images are jointed to form a complete original pathological section image. However, since high resolution digital images obtained by scanning a microscope and an optical amplification system are prone to be affected by surrounding environment or the microscope per se, the resolutions of the digital images obtained by scanning have discrepancy, some of the digital images are clear, while some of the digital images are vague. Therefore, the accuracy of the complete original pathological section image formed by jointing each of the digital pathological images is not so high. In this case, a second detection unit B2 is provided in the image processing end B for detecting the definition of jointing region in the original pathological section image where a plurality of digital pathological images are jointed to one another, and the image detected to be unqualified will not be transmitted to the remote server C.

In this embodiment, the second detection unit B2 can also be formed by a second processor in the image processing end B, that is, the second processor is adopted to detect the definition of the jointing region in the original pathological section image where a plurality of digital pathological images are jointed to one another.

In this embodiment, the first processor and the second processor can be integrated in the same processing chip of the image processing end B, that is, the same processing chip is used to simultaneously detect the brightness of the image and the definition of the jointing region. Accordingly, the first processor and the second processor can also be set alone and work independently.

In this embodiment, with respect to the original pathological section image formed by a single digital pathological image, the definition of the jointing region may not be detected by the second detection unit B2.

In this embodiment, an output unit B3 is used to output the original pathological section image that has been detected to be qualified by the first detection unit B1 and the second detection unit B2. Specifically, the output unit B3 may be a communication interface in the image processing end B and configured to send the digital pathological section image having been processed (detection of brightness/detection of definition of jointing region) to the remote server C via remote communication (e.g., wired/wireless communication).

In this embodiment, patients' trust to different attending physicians may vary, for example, patients trust more to attending physicians who have some experience and have handled more complicated cases, and trust much less to attending physicians who relatively lack experience and be nameless among the public. In view of this, in the technical scheme of the present invention, there is provided a system function which allows the patients to choose the attending physician to read the digital pathological section image.

Specifically, the first client end D is a client end to be used by the patient, and the second client end E is a client end to be used by the attending physician. The scanning end A allows the first client end D associated with the pathological section to upload the medical record information to the remote server C while scanning the pathological section and uploading the corresponding digital pathological section image to the remote server C. The medical record information may include the attending physician information selected by the patient through the first client end D. Of course, the medical record information may also include general information such as the patient's own physical signs information and preliminary diagnostic information.

A plurality of storage units C11 are provided in the storage space C1 of the remote server C, each storage unit C11 corresponds to one attending physician information. Specifically, one storage unit C11 can be regarded as a specific storage path corresponding to specific attending physician information. If the patient designates one attending physician as the physician of the patient, and after it is confirmed by the designated physician, the patient will send the medical record information including the designated attending physician information to the remote server C through the first client end D, and the remote server C will obtain the corresponding attending physician information according to the medical record information, and save the digital pathological section image (associating the pathological section with the corresponding patient before it is examined by the scanning end A) corresponding to the patient in the storage unit C11 corresponding to the designated attending physician.

In this embodiment, when the attending physician needs to browse the digital pathological section image, the attending physician logs into the remote server C through the second client end E, then the remote server C will be accessed by the physician, and the physician can view the digital pathological section image stored in his corresponding storage unit C11. The attending physician may choose to browse the digital pathological section image online at the remote server C. Alternatively, the attending physician may download the digital pathological section image to the second client end E to browse offline.

In this embodiment, a mobile terminal or other computer device may function as the first client end D. The second client end E may be an end with a certain processing capability and capable of providing the attending physician with normal browsing of the digital pathological section image.

Figure 2:
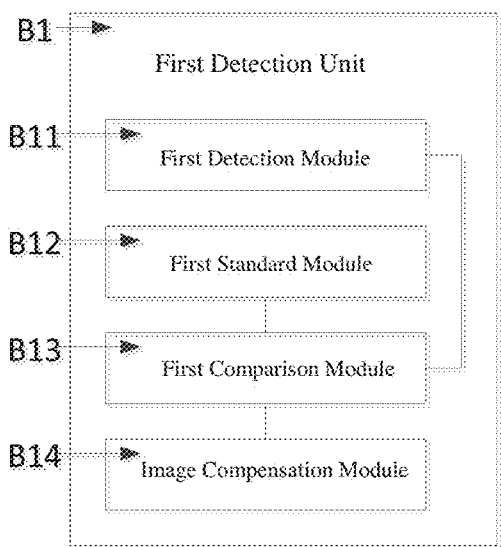
FIG. 2 is a schematic diagram of a specific structure of a first detection unit on the basis of FIG. 1 in a preferred embodiment of the present invention.

In a preferred embodiment of the present invention, as shown in FIG. 2, wherein the first detection unit B1 specifically comprises:

a first detection module B11, for detecting a brightness value of the original pathological section image;

a first standard module B12, providing a preset brightness range of a standard image corresponding to the original pathological section image;

a first comparison module B13, connected to the first detection module B11 and the first standard module B12, respectively, for comparing the brightness value of the original pathological section image with the brightness range of the standard image;

outputting the first detection result indicating that the brightness value of the original pathological section image is qualified when the brightness value of the original pathological section image is within the brightness range of the standard image, and outputting the first detection result indicating that the brightness value of the original pathological section image is unqualified when the brightness value of the original pathological section image falls outside the brightness range of the standard image.

The first detection unit B1 will now be described with the aid of a specific embodiment: an existing label graph to be determined, the brightness value thereof is detected to be 164.097 by the first detection module B11; the preset standard image in the first standard module B12 has brightness in the range of 175-230. The first comparison module B13 compares the brightness value of 164.097 of the original pathological section image to be determined with the brightness range of 175-230 of the preset standard image, then it is determined that the brightness value of the original pathological section image falls outside the brightness range of the standard image. Therefore, the first comparison module B13 outputs a first detection result, indicating the original pathological section image is unqualified.

In the above embodiment, the brightness of the image to be determined is compared with the brightness range of the standard image. When the brightness of the image to be determined is within the brightness range of the standard image, the brightness of the image is qualified. Otherwise, the brightness of the image is unqualified. Such determination of the brightness of image does not depend on people's subjective judgment, which not only avoids the judgment error caused by the subjective factors, but also improves the work efficiency due to judgment automatically made by the system.

In a preferred embodiment, still as shown in FIG. 2, wherein the first detection unit B1 further comprises:

an image compensation module B14, connected to the first comparison module B13, wherein, when the first comparison module B13 outputs the first detection result indicating the brightness value of the original pathological section image is unqualified, the image compensation module B14 outputs an illumination compensation instruction based on a difference between the brightness value of the unqualified original pathological section image and the brightness range of the standard image, then the image processing end B feeds back the illumination compensation instruction to the scanning end A to obtain the original pathological section image by controlling the scanning end A to rescan the pathological section.

Specifically, in this embodiment, the image compensation module B14 connects with the first comparison module B13, when the first comparison module B13 detects an unqualified image, the image compensation module B14 outputs an illumination compensation instruction for the unqualified image based on a difference between the brightness value of the unqualified image and the brightness range of the standard image. The scanning end A, according to this specific operating instruction, controls its illumination light source (which will be explained hereinafter) to perform the corresponding illumination compensation operation, so as to obtain an original pathological section image by rescanning.

In a preferred embodiment, the image processing end B further comprises an alarm unit B1 (not shown) connected to the first detection unit B1. When the first comparison module B13 detects that the brightness of certain original pathological section image is unqualified (i.e., the brightness value is not within the preset brightness range), the alarm unit will give an alarm to prompt an operator to rescan the pathological section to obtain an original pathological section image.

In a preferred embodiment of the present invention, after obtaining the original pathological section image by rescanning, the operator still sends the original pathological section image to the first detection unit B1 and the second detection unit B2 to be detected.

In a preferred embodiment of the present invention, the original pathological section image may be a section image which is obtained by scanning the pathological section and may also be a blank section image. That is, the first detection unit B1 may also be used to determine whether the blank section image is qualified or not. Supposing that a background image of a blank section obtained by scanning is provided, and background brightness of the image is detected to be 234.891. A standard image, having a preset background brightness in the range of 230-252, is provided. It can be determined by the first detection unit B1 in the technical schemes of the present invention that the background brightness of the scanned blank section is within the range of the standard image, therefore, the background image of the blank section is qualified.

Similarly, this embodiment can also be used to determine whether the background image of the detected pathological section is within the qualified range, that is, the first detection unit B1 may detect whether the brightness of the part where the section tissue in the original pathological section image is located is qualified, and simultaneously detect whether the brightness of the background in the original pathological section image is qualified. The first detection unit B1 determines that the brightness of the original pathological section image is qualified in condition that both of the two are qualified.

In conclusion, the working principle of determining the brightness value of the original pathological section image by using the first detection unit B1 provided by the technical scheme of the present invention specifically comprises:

measuring the brightness value of the image first;

then, providing a preset brightness range value of the standard image corresponding to the image;

subsequently, determining whether the brightness value of the image is within the brightness range of the standard image: if the brightness value of the image is within the brightness range of the standard image, it is determined that the image is qualified; if the brightness value of the image is not within the brightness range of the standard image, it is determined that the image is unqualified.

Figure 3:
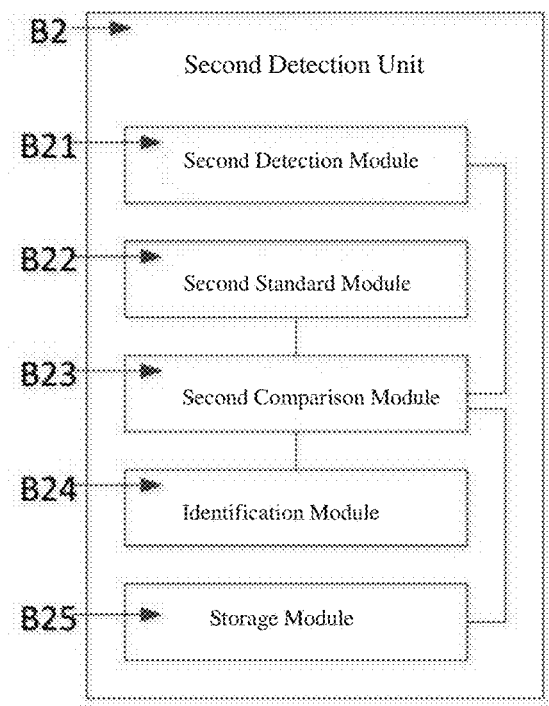
FIG. 3 is a schematic diagram of a specific structure of a second detection unit on the basis of FIG. 1 in a preferred embodiment of the present invention.

In a preferred embodiment, as shown in FIG. 3, wherein the second detection unit B2 specifically comprises:

a second detection module B21, processing the two digital pathological images that are jointed to each other, to obtain an image gradient of one digital pathological image to serve as a first gradient value, and to obtain an image gradient of the other digital pathological image to serve as a second gradient value;

a second standard module B22, providing a preset gradient ratio in advance;

a second comparison module B23, connected to the second detection module B21 and the second standard module B22, respectively, for comparing the ratio of the first gradient value to the second gradient value with the preset gradient ratio, and when the ratio is not matched with the preset gradient ratio, it is determined that the definition of the jointing region where the two digital pathological images are jointed to each other is unqualified, and thus outputting the second detection result indicating the definition of the jointing region where the original pathological images are jointed to each other is unqualified.

Figure 4:
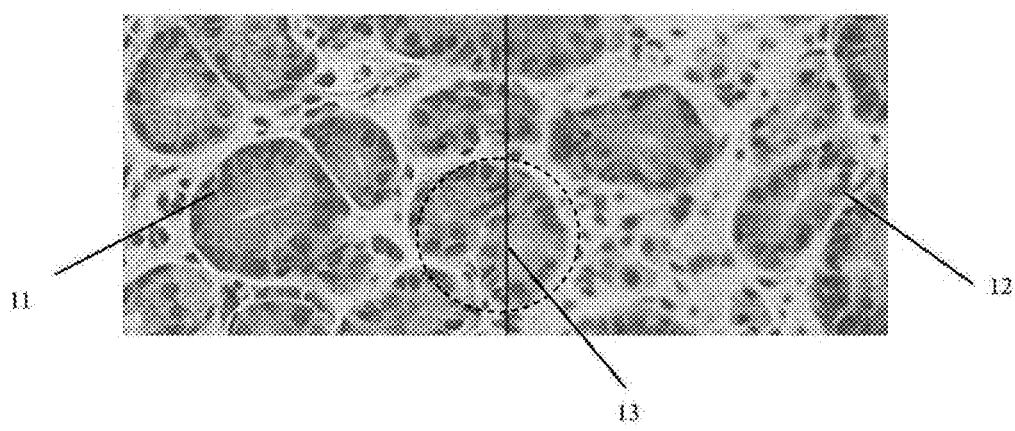
FIG. 4 is a schematic diagram of an original pathological section image jointed by a plurality of digital pathological section images in a preferred embodiment of the present invention.

In this embodiment, the original pathological section image is formed by jointing at least two digital pathological section images. An original pathological section image jointed by one digital pathological image 11 and another digital pathological section image 12 is shown in FIG. 4 as an example for the illustration of the technical schemes of the present invention.

A digital pathological section image 11 and a digital pathological section image 12 are jointed to each other, and therefore, it can be seen that the same cellular tissue may be displayed on the jointing region 13 in the digital pathological section image 11 and the digital pathological section image 12. In order to ensure the definition of the cells at the jointing region 13 is the same, the focus of the present invention is on how to determine whether the definition at the jointing region of these two digital pathological images is qualified or not. Further, at least one jointing region 13 exists in an original pathological section image, while in this embodiment, only one jointing region 13 is taken as an example for illustration.

In this embodiment, the second detection module B21 obtains the gradient value of the digital pathological image 11 to function as the first gradient value and obtains the gradient value of the digital pathological image 12 to function as the second gradient value. Before that, the second standard unit B22 provides a preset gradient ratio, which may be preset according to the overall definition of the original pathological section image or may be set by the user according to the actual situation. The second comparison module B23 compares the ratio of the first gradient value to the second gradient value with the preset gradient ratio:

when the ratio of the first gradient value to the second gradient value does not match with the preset gradient ratio, the second comparison module B23 determines that the definition of the jointing region 13 between the two digital pathological images that are jointed to each other is unqualified;

accordingly, when the ratio of the first gradient value to the second gradient value matches with the preset gradient ratio, the second comparison module B23 determines the definition of the jointing region 13 between the two digital pathological images that are jointed to each other is qualified.

The above definition judgment method can objectively judge the quality of an image, which not only avoids the defect of inconsistent evaluation result due to people's subjective factors, but also reduces the workload of the operator involved in evaluating the image quality.

In a preferred embodiment of the present invention, wherein when the first gradient value is less than or equal to the second gradient value, the preset gradient ratio is less than or equal to 1;

then the second comparison module B23 compares the ratio of the first gradient value to the second gradient value with the preset gradient ratio, and according to the comparison result, when the ratio of the first gradient value to the second gradient value is less than the preset gradient ratio, it is determined that the definition of the spliced section where the two digital pathological images are spliced to each other is unqualified;

when the ratio of the first gradient value to the second gradient value is greater than or equal to the preset gradient ratio, it is determined that the definition of the jointing region where the two digital pathological images are spliced to each other is qualified.

In a preferred embodiment of the present invention, wherein when the first gradient value is greater than the second gradient value, the preset gradient ratio is greater than 1;

then the second comparison module compares the ratio of the first gradient value to the second gradient value with the preset gradient ratio, and according to the comparison result, when the ratio of the first gradient value to the second gradient value is greater than or equal to the preset gradient ratio, it is determined that the definition of the jointing region where the two digital pathological images are jointed to each other is unqualified;

when the ratio of the first gradient value to the second gradient value is less than the preset gradient ratio, it is determined that the definition of the jointing region where the two digital pathological images are jointed to each other is qualified.

Specifically, several cases in which the definition of the jointing region 13 between two digital pathological images that are jointed to each other is determined to be qualified or unqualified:

1) when the first gradient value is less than or equal to the second gradient value, the smaller the ratio of the gradient value of the two digital pathological images, the greater the difference of the definition between the two digital pathological images; when the ratio is less than the preset gradient ratio, it indicates that the definitions of the two digital pathological images are unqualified. Therefore, the case that the ratio of the first gradient value to the second gradient value matches with the preset gradient ratio, means that the ratio is greater than or equal to the preset gradient ratio.

2) when the first gradient value is greater than the second gradient value, the greater the ratio of the gradient value of the two digital pathological images, the greater the definitions of the two digital pathological images; when the ratio is greater than or equal to the preset gradient ratio, it indicates that the definitions of the two digital pathological images are unqualified. Therefore, the case that the ratio of the first gradient value to the second gradient value matches with the preset gradient ratio, means that the ratio is less than the preset gradient ratio.

In a preferred embodiment of the present invention, still as shown in FIG. 3, wherein the second detection unit B2 further comprises:

an identification module B24, connected to the second comparison module B23, for identifying the jointing region on the digital pathological image where the second comparison module determines the definition of the digital pathological image is unqualified.

Specifically, in this embodiment, after unqualified jointing region 13 is determined, it can be marked at the unqualified jointing region 13 in a different manner, for example, a circular dotted box, or a square box, or a colored mark and so on. An additional detection system may also be used to set a serial number for each jointing region. When a jointing region 13 is detected as unqualified, the serial number corresponding to the jointing region 13 is displayed in the detection system. In this embodiment, a circular dotted box is used to identify the jointing region 13 with unqualified definition, as shown in FIG. 4.

In a preferred embodiment of the present invention, even though one part of the jointing region is not clear to see, it does not necessarily mean that the whole original pathological image is unqualified. Specifically, after the identification module B24 identifies the jointing region 13 of the digital pathological section image in which the definition is unqualified, whether to use the digital pathological section or not depends on how bad the digital pathological image is. For example, when the number of unqualified jointing region 13 indicated in the digital pathological section exceeds a preset number (which may be three or five or set by the user according to the actual situation), it is determined that the whole original pathological image is unqualified, and rescanning and redetection of the digital pathological section is needed. Conversely, as long as the number of unqualified jointing region 13 does not exceed the preset number, it is still considered that the original pathological section image can be used, that is, the original pathological section image is deemed to be qualified as a whole.

In a preferred embodiment of the present invention, still as shown in FIG. 3, wherein the second detection unit B2 further comprises:

a storage module B25, connected to the second comparison module B23, for temporarily storing the digital pathological image whose definition is determined to be qualified by the second comparison module.

In conclusion, in the technical scheme of the present invention, the working principle of the second detection unit B2 for detecting the definition of jointing region of the original pathological section image formed by jointing a plurality of digital pathological images specifically comprises:

first, processing the two digital pathological images that are jointed to each other to obtain an image gradient of a digital pathological image 11 to function as a first gradient value, and to obtain an image gradient of a digital pathological image 12 to function as a second gradient value;

second, comparing the ratio of the first gradient value to the second gradient value with the preset gradient ratio, and when the ratio is not matched with the preset gradient ratio, it is determined that the definition of the jointing region 13 where the two digital pathological images are jointed to each other is unqualified.

In a preferred embodiment of the present invention, wherein in the digital pathological section scanning system, section-cutting can be performed on the human tissue of the same person, and two different original pathological section images are formed by scanning via the scanning end;

in the image processing end B, the scanning system respectively detects the brightness value and the definition of the jointing section of the two original pathological section images, and forms two digital pathological section images respectively corresponding to the two original pathological section images, serving as a first section image and a second section image;

wherein, the first section image is located in a first XOY coordinate axis which functions one endpoint of the first section image as an original point, and the second section image is located in a second XOY coordinate axis which functions one endpoint of the second section image as an original point;

then still as shown in FIG. 1, the image processing end B further comprises:

an adjusting unit B4, connected to the output unit B3, for adjusting, before the digital pathological section image is sent out by the output unit, the second section image according to the relative position between the first section image and the second section image, and integrating the adjusted second section image and the first section image into a corresponding digital pathological section image to be sent to the remote server by the output unit.

Specifically, in this embodiment, in clinical diagnosis, the case that the same tissue is sectioned and stained with different stains is often presented, and thus the position and angle of the tissue in several section images may be different, and physicians often need to compare a plurality of section images of the same tissue when browsing section images, and compare the image information in the same position to obtain more accurate diagnosis result. It is common practice to add a single image angle rotation function to the related software for digital section browsing, and this function is done manually, such that the plurality of section images can be adjusted to be consistent by observation with naked eyes and by manual adjustment. The above-mentioned method is time-consuming and labor-intensive, and there are many problems that the manual adjustment has a slow adjustment speed and poor adjustment accuracy, thereby affecting the subsequent diagnosis result and reducing the physician's working efficiency. Hence, in the technical scheme of the present invention, the adjusting unit B4 is provided to achieve the purpose of automatic rotation matching of the digital pathological sections.

In a preferred embodiment of the present invention, the adjusting unit B4 can be formed by using the third processor in the image processing end B, that is, achieving the function of the adjusting unit B4 by using a third processor.

In a preferred embodiment of the present invention, the third processor may also be integrated with the first processor and the second processor in a processing chip. Accordingly, the above three processors can also be set alone and work independently.

Figure 5:
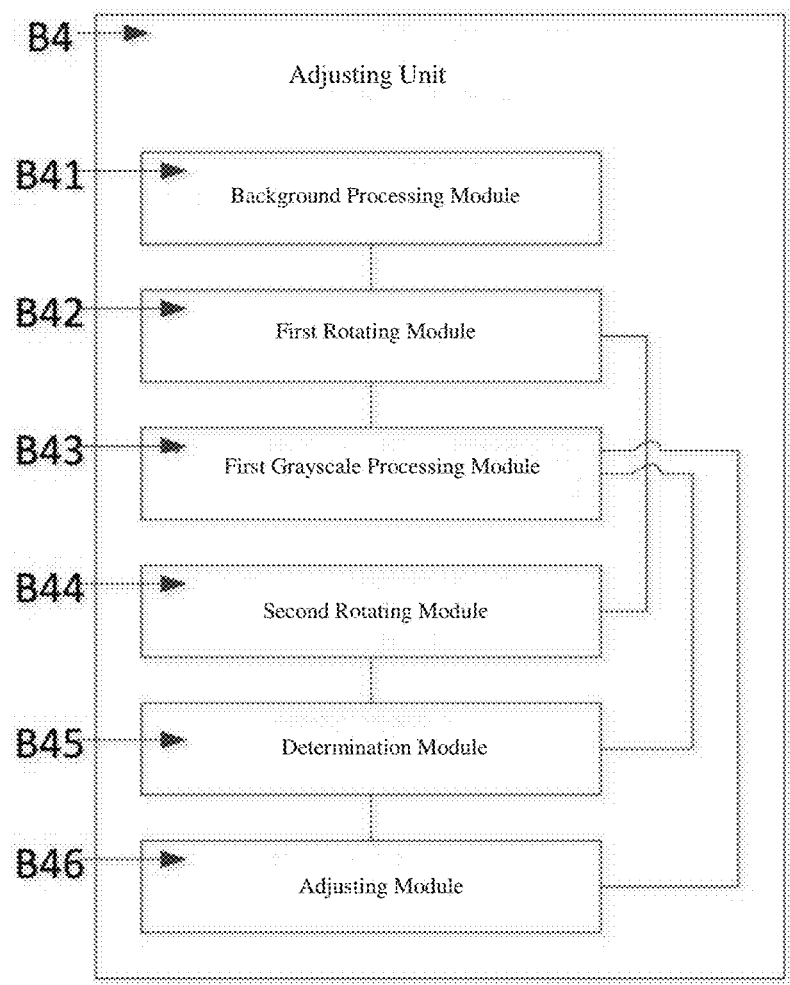
FIG. 5 is a schematic diagram of a specific structure of an adjusting unit on the basis of FIG. 1 in a preferred embodiment of the present invention.

Further, in a preferred embodiment of the present invention, as shown in FIG. 5, wherein the adjusting unit B4 specifically comprises:

a background processing module B41, for expanding the outline size of the first section image, and filling the enlarged portion of the first section image with a blank background;

a first rotating module B42, connected to the background processing module B41, for aligning the endpoint in the second section image, coinciding with the original point of the second XOY coordinate axis, with a preset rotating point in the first section image;

a first grayscale processing module B43, connected to the first rotating module B42, for processing the first section image to obtain a gray value of a preset first determination point, and processing the second section image to obtain a gray value of a second determination point corresponding to the first determination point, followed by obtaining a grayscale comparison value under the current relative position between the first section image and the second section image;

a second rotating module B44, connected to the first rotating module B42, for rotating the second section image clockwise about the endpoint coinciding with the original point of the second XOY coordinate axis by a preset angle;

a determination module B45, connected to the first grayscale processing module B41 and the second rotating module B44 respectively, for determining, after the second rotating module rotates the second section image, whether the second section image has rotated about 360 degrees relative to an initial position, and outputting a determination result;

wherein, the first grayscale processing module B41 is further configured to perform, according to the determination result, the grayscale processing again when the second section image has not rotated about 360 degrees relative to the initial position;

and the second rotating module B44 is further configured to continue rotating, according to the determination result, the second section image when the second section image has not rotated about 360 degrees relative to the initial position;

an adjusting module B46, connected to the first grayscale processing module B41 and the determination module B45, respectively, for obtaining, according to the determination result, the gray value with the smallest value when the second section image has rotated about 360 degrees relative to the initial position, and adjusting the second section image according to the relative position between the first section image and the second section image corresponding to the obtained grayscale value.

Figure 6:
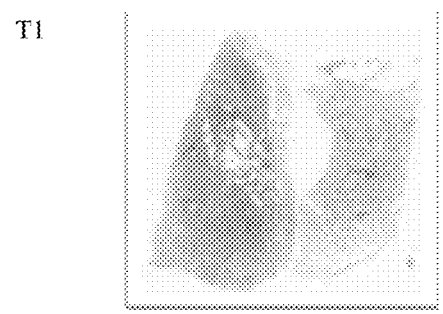
FIGS. 6-8 are schematic diagrams of adjusting section images by rotation in a preferred embodiment of the present invention.
Figure 7:
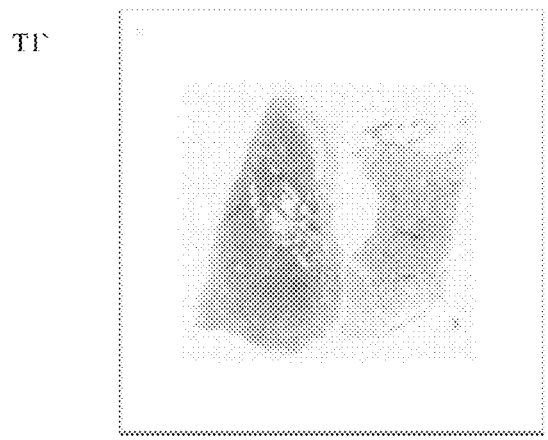

Specifically, in this embodiment, firstly, the outline of the first section image is enlarged by using the background processing module B41 and is filled with a blank background in the enlarged portion. For example, the initial first section image T1 is shown in FIG. 6, and the enlarged first section image T1' is shown in FIG. 7, it can be seen from FIGS. 6 and 7 that it does not enlarge the whole first section image T1, but only enlarges the outline. Therefore, in the enlarged first section image T1', the body portion thereof (the portion of the initial first section image T1) has not been enlarged, and thus in the first section image T1', the section tissue of the first section has not been distorted by stretching, and the enlarged portion is filled with blank background, to form the enlarged first section image T1' as shown in FIG. 7.

In this embodiment, after enlarging the first section image, the first rotating module B42 is used to align the endpoint of the second section image, coinciding with the original point of the second XOY coordinate axis, with a preset rotating point in the enlarged first section image. Specifically, the endpoint of the second section image coinciding with the original point of the second XOY coordinate axis is the endpoint of coordinates (0, 0) in the second XOY coordinate axis, which aligns with the preset rotating point in the enlarged first section image. After alignment, it does not need to pay attention to the current relative position between the first section image and the second section image, that is, it does not need to pay attention to the angle between the first section image and the second section image.

In this embodiment, the first grayscale processing module B43 is used to obtain a gray value of a preset first determination point on the enlarged first section image and to obtain a gray value of the second determination point on the second section image corresponding to the first determination point.

Specifically, that the second determination point corresponds to the first determination point means that when the endpoint of the second section image aligns with the preset rotating point of the first section image, the second section image is overlapped with the first section image, and the second determination point is a point coinciding with the first determination point. For instance, if the coordinate of the first determination point in the first section image is (i+m, j+n) in the first XOY coordinate axis, the coordinate of the second determination point in the second section image is (i,j) in the second XOY coordinate axis, then the position of the second determination point coincides with that of the first determination point. Subsequently, the gray value at the first determination point and the gray value at the second determination point are obtained respectively by calculating, and the grayscale comparison value under the current position is obtained by calculation.

In this embodiment, after the above-mentioned grayscale comparison value is obtained by calculation, the second rotating module B44 is used to rotate the second section image clockwise about the endpoint coinciding with the original point of the second XOY coordinate axis by a preset angle. After the rotation, the determination module B45 is used to determine whether the second section image has rotated about 360 degrees. If not, keep rotating the second section image by using the second rotating module B44 and judge the second section image by using the determination module B45, till the second section image has rotated over 360 degrees. In a preferred embodiment of the present invention, the preset angle in Step S4 may be 1 degree, that is, the second section image is judged when it is rotated by 1 degree each time until it is rotated about 360 degrees in the clockwise direction.

In this embodiment, after the second section image is rotated clockwise about 360 degrees, the corresponding grayscale comparison value is obtained after rotating every preset angle (e.g., rotate about 1 degree each time), and a adjusting module B46 is used to extract the smallest grayscale comparison value among all of the grayscale comparison values, and adjusting the second section image according to the relative position between the first section image and the second section image corresponding to the obtained grayscale value. Specifically, acquiring an adjustment scheme for the second section image according to the rotation angle of the second section image corresponding to the extracted grayscale comparison value and the initial position of the second section image, and adjusting the second section image, wherein, the initial position refers to a position where the endpoint of the second section image does not coincide with the preset rotating point of the first section image, that is, a position where the second section image is placed in the same direction as the first section image (refers to FIGS. 6 and 8). For example, if the rotation angle of the second section image corresponding to the extracted grayscale comparison value is 180 degrees, the adjustment scheme is as follows: rotating the second section image clockwise about 180 degrees based on the initial position of the second section image.

In a preferred embodiment of the present invention, wherein the background processing module B41 enlarges the first section image to an image with a width and a height of A, and fills the enlarged portion of the first section image with a blank background;

wherein.

$$A = \sqrt[2]{W_1^2 + H_1^2}$$

$W_1$ represents the width of the first section image;
$H_1$ represents the height of the first section image.

Specifically, in this embodiment, the size of the first section image and the size of the second section image may not be the same, wherein $W_1$ represents the width of the first section image, and $H_1$ represents the height of the first section image; accordingly, $W_2$ represents the width of the second section image, and $H_2$ represents the height of the second section image, and the above settings are available hereinafter.

Then the above-mentioned background processing module B41 is used to enlarge the first section image to a rectangle graph with a width A and a height A, the value of A is obtained according to the above-mentioned formula (1), and the enlarged portion is filled with a blank background. Specifically, the first section image T1 before enlargement is as shown in FIG. 6, and the enlarged first section image T1' is as shown in FIG. 7.

Figure 9:
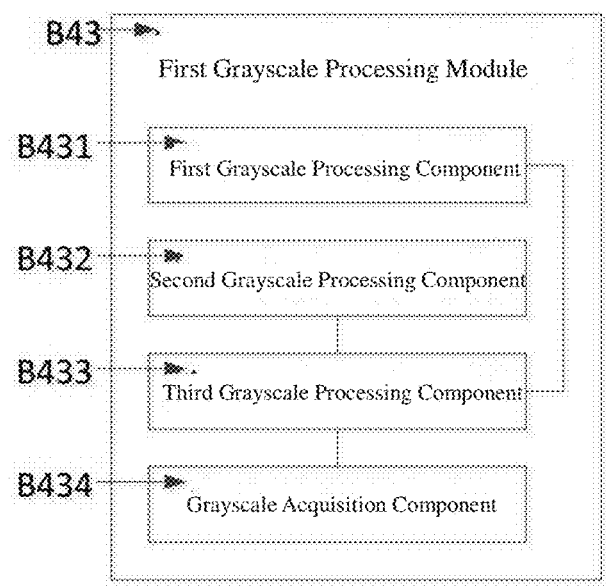
FIG. 9 is a schematic diagram of a specific structure of a first grayscale processing module on the basis of FIG. 5 in a preferred embodiment of the present invention.

In a preferred embodiment of the present invention, wherein the value range of the coordinate (m, n) of the preset rotating point satisfies the follows:

$$0 \le m < W_1 - W_2; \tag{2}$$

$$0 \le n < H_1 - H_2; \tag{3}$$

wherein, m represents the X-axis coordinate of the preset rotating point in the first XOY coordinate axis;

n represents the Y-axis coordinate of the preset rotating point in the first XOY coordinate axis;

In a preferred embodiment of the present invention, wherein the preset coordinate of the first determination point has a preset value range;

then as shown in FIG. 9, the first grayscale processing module B43 further comprises:

a first grayscale processing component B431, for processing the first section image to obtain a gray value of each of the first determination point within the value range, to serve as a first grayscale value;

a second grayscale processing component B432, for processing the second section image to obtain a gray value of each of the second determination point corresponding to each of the first determination point within the value range, to serve as a second grayscale value;

a third grayscale processing component B433, connected to the first grayscale processing component B431 and the second grayscale processing component B432, respectively, for obtaining, according to the first gray value and the corresponding second grayscale value, each corresponding grayscale comparison value respectively;

a grayscale acquisition component B434, connected to the third grayscale processing component B433, for obtaining the grayscale comparison value with the smallest value, serving as the grayscale comparison value under the current relative position between the first section image and the second section image.

Specifically, in this embodiment, the first determination point can be represented as $P_1(i+m, j+n)$, and the second determination point can be represented as $P_2(i, j)$. Then:

$$0 \le i < W_2; \tag{4}$$

$$0 \le j < H_2; \tag{5}$$

Then it can be learned in combination with the above formulas (2) and (3) that:

the second judgment point has a value in the range of (0, 0) to ($W_1$, $H_1$).

Figure 8:
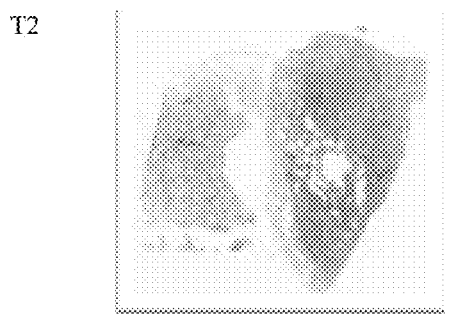

In other words, it is necessary to ensure that the first determination point is located within the range of the first section image T1 and the second determination point is located within the range of the second section image T2 (as shown in FIG. 8), and the position of the first determination point and the that of the second determination point corresponds to each other.

Subsequently, in this embodiment, the gray value of each of the selected first determination points and the corresponding second determination points is obtained respectively. The gray value of the first determination point is regarded as a first grayscale value, and the gray value of the second determination point is regarded as a second grayscale value. Subsequently, a grayscale comparison value of the selected first determination point and the second determination point is obtained according to the first gray value and the second grayscale value.

Further, in a preferred embodiment of the present invention, the grayscale comparison value is obtained according to the following formula:

$$S(m,n)=\sum_{i=0, j=0}^{i=W_2-1, j=H_2-1}|P_1-P_2| \qquad (6)$$

wherein,

S(m,n) represents the grayscale comparison value between $P_1$(i+m, j+n) and $P_2$(m, n);

Subsequently, the first determination point and the corresponding second determination point in the value range are cyclically processed for the grayscale comparison value, and among all the grayscale comparison values obtained, the one having the smallest value is finally obtained as the grayscale comparison value S(m,n) under the current position. In a preferred embodiment of the present invention, the relative position between the first section image and the second section image may be represented by a rotation angle by which rotation is done clockwise about the endpoint of the second section image coinciding with the endpoint of the first section image. Therefore, the above-mentioned grayscale comparison value S (m,n) can also be represented as S (ag), wherein, ag represents the current rotation angle of the second section image.

Therefore, in a preferred embodiment of the present invention, each time the second section image rotates by a preset angle, the grayscale comparison value in the state of the rotation angle is obtained. For example, when the second section image rotates clockwise to 30 degrees, a grayscale comparison value S (30°) is obtained by calculation, and when the second section image rotates clockwise to 60 degrees, the grayscale comparison value S (60°) is obtained by calculation, and so on. That is, in the grayscale acquisition component B434, after the grayscale comparison value with the smallest value is obtained, and the obtained grayscale comparison value is regarded as the grayscale comparison value under the relative position between the first section image and the second section image, the rotation angle of the second section image under the current relative position relative to the initial position is recoded.

In a preferred embodiment of the present invention, still as shown in FIG. 1, wherein a preview of the pathological section is obtained first by pre-scanning before the scanning end A scans the pathological section;

the image processing end B further comprises:

an identification unit B5, for recognizing the preview to obtain a section tissue image in the preview;

the image processing end B transmits the section tissue image back to the scanning end A, and the scanning end A scans the pathological section according to the section tissue image.

Specifically, before scanning the section, the preview of the section needs to be processed in advance, the tissue is accurately identified, and the related information (that is, the region where the section tissue exists) is extracted, so as to make the scanning more accurate and effectively reduce the blank part included in the final digital pathological section image, and to increase the physician's efficiency in the identification of the section image.

In this embodiment, before the scanning end scans the section tissue, it roughly scans the section tissue and forms a preview thereof, and sends the preview to the image processing end B. At the same time, an identification unit B5 is provided in the image processing end B, and the identification unit B5 is configured to identify the area where the section tissue exists in the image according to the preview transmitted from the scanning end A, and the identification unit B5 keeps the area where the section tissue is located and deletes other areas, so as to form a section tissue image and send the section tissue image back to the scanning end A. The scanning end A finally performs a formal scanning of the pathological section according to the section tissue image, that is, only the part of the section tissue corresponding to the section tissue image is scanned to form a corresponding original pathological section image and the corresponding original pathological section image is transmitted to the image processing end B for further processing.

In a preferred embodiment of the present invention, the identification unit B5 may be a fourth processor disposed in the image processing end B, that is, the fourth processor may be used to achieve the function of the identification unit B5. The fourth processor may be integrated with the first processor, the second processor, and the third processor in the same processing chip, or may be set alone and work independently, and which will not be repeated herein.

Figure 10:
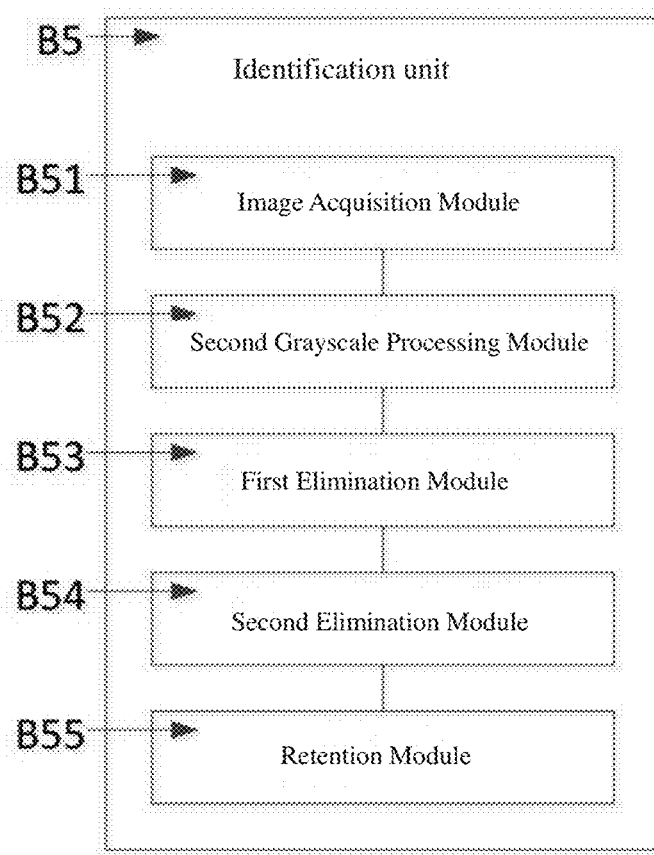
FIG. 10 is a schematic diagram of a specific structure of an identification unit on the basis of FIG. 1 in a preferred embodiment of the present invention.

In a preferred embodiment of the present invention, wherein a blank section image is obtained by scanning the blank slide via the scanning end A in advance;

then as shown in FIG. 10, the identification unit B5 specifically comprises:

an image acquisition module B51, obtaining a background image of the blank section image and the preview, respectively;

a second grayscale processing module B52, connected to the image acquisition module B51, for subtracting the gray value of the background image from the gray value of the preview to obtain a section information graph;

a first elimination module B53, connected to the second grayscale processing module B52, for performing traversal processing on the connected domains of the section information graph, and eliminating stains in the section information graph;

a second elimination module B54, connected to the first elimination module B53, for respectively judging, according to the attribute of the connected domain, whether each connected domain in the section information graph having been eliminated the stains is a section tissue, and eliminating the connected domain which is not the section tissue;

a retention module B55, connected to the second elimination module B54, for retaining the section information graph as the section tissue image after the connected domain which does not belong to the section tissue is eliminated.

In the prior art, the image processing technology is commonly used to carry out gray-scale processing on the preview, and to discriminate the tissue, the background, the impurities of the section or stains from section according to the brightness difference, so as to identify and extract the tissue part. This method is generally for identification of one or several specific types of section tissues, not applicable to most of the sections. And the case that the tissue is omitted, and that the impurities and the stains are mistakenly identified as the tissue is often exist during the traditional way of brightness recognition, which makes it almost impossible to achieve an accurate identification, thus reducing the accuracy and the efficiency of identifying the section tissue.

In this embodiment, the tissue part is effectively identified as possible by discriminating the tissue and impurities in characteristics such as color and geometric shape. At the same time, a majority of the impurities and the stains are identified and eliminated, thereby separating the tissue part in the section preview in a more accurate way.

Specifically, the working principle of the identification unit B5 is as follows:

first, scanning the background image of the blank section and the preview of the tissue section to be identified;

second, subtracting the gray value of background image from the gray value of the preview, and obtaining a section information graph;

then, performing a traversal processing on the connected domain, and eliminating stains in the section information graph;

subsequently, respectively judging whether each connected domain in the section information graph is the section tissue according to the attribute of the connected domain, and eliminating the connected domain which is not the section tissue;

finally, retaining the section information graph with the connected domain eliminated which are judged as not section tissue to be output as a section tissue image.

In a preferred embodiment of the present invention, the second elimination module B54 may judge the section tissue according to one or more rules described below:

1) the elimination module B54 can find the connected domain with the largest area among the remaining connected domains in which the stains have been eliminated from the section information graph, and an area difference is obtained by subtracting the area of the remaining connected domains from the area of the connected domain with the largest area, and the connected domain whose area difference is within a preset area difference range is judged to be the section tissue.

On the one hand, area of the impurities is relatively smaller, and the area of the tissue is relatively larger, therefore, it can be judged whether the impurities and the tissue are section tissues by discriminating their geometric shapes. On the other hand, before scanning the tissue, it is necessary to render color to the tissue section by using dye, so as to make the dye interact with a certain component in the tissue or the cell. It is absorbed and refracted by a spectrum to make its various fine structures show different colors, such that various components of the tissue cells can be shown under the microscope. In addition, most of the impurities are yellow, so it can be judged whether the impurities are section tissues according to the difference in color between the impurities and the tissue cells. For example, find the connected domain with the largest area among the connected domains with the stains eliminated, and compare another connected domain with the area of the connected domain with the largest area, to obtain an area difference. If the area difference is within the preset area difference range, it illustrates that the area of another connected domain is also relatively large, so another connected domain can be judged to be the connected domain.

2) The above mentioned second elimination module B54 can calculate the color mean of the RGB channels of the remaining connected domains after the stains in the section information graph have been eliminated, and obtain the corresponding RGB difference according to the color value of the RGB channels of the remaining connected domains and the color mean of the RGB channels, and the connected domain corresponding to the RGB difference of the same connected domain within a preset RGB difference range is judged as the section tissue.

In the color judgment rule, adding up the total color value of the R channel, the total color value of the G channel and the total color value of the B channel of all the connected domains, and obtaining the mean value of the R channel, the mean value of the G channel and the mean value of the B channel of all the connected domains. When the R color value, G color value and the B color value of the remaining connected domains to be judged is quite different from the mean value of the R channel, the mean value of the G channel and the mean value of the B channel to be calculated, for example, if the RGB difference of the same connected domain is within a preset RGB difference range, the remaining connected domains are judged as dyed tissues. When the R color value, G color value and the B color value of the remaining connected domains to be judged is not quite different from the corresponding mean value of the R channel, the mean value of the G channel and the mean value of the B channel to be calculated, for example, if the RGB difference of the same connected domain is not within the preset RGB difference range, the remaining connected domains are judged as impurities.

3) The second elimination module B54 can determine that the connected domain in the section information graph that is in contact with the edge of the section information graph is not the connected domain of the section tissue.

This rule may be referred to as edge-touching judgment rule, which judges whether the connected domain is in contact with the edge of the section information graph, and if yes, it is determined as the impurity.

4) The second elimination module B54 can determine the connected domain among the remaining connected domains, in which the stains in the section information graph have been eliminated and the brightness value is within a preset brightness range, as the connected domain of the section tissue.

Since the brightness value of the impurity and the tissue is different, the impurity can be differentiated from the tissue based on their respective brightness value.

Embodiments of four rules have been listed above upon which the second elimination module B54 can determine the section tissue, in the present invention, one or more embodiments can be applied to the second elimination module B54. For example, a domain that meets at least two of the above four rules may be determined as a connected domain in which a section tissue exits, and finally a section tissue image is generated. In order to improve accuracy, the four above rules can be applied at the same time, that is, the domain that meets the above four rules is selected as the connected domain in which the section tissue exists, and thus, the section tissue image is generated and output.

In a preferred embodiment of the present invention, the first elimination module B53 may apply at least one of the elimination rules listed below to eliminate stains in the section information graph, specifically comprising:

eliminating the connected domain having an area less than a preset area;

eliminating the connected domain having a length-to-width ratio less than a preset length-to-width coefficient; and eliminating the connected domain having an area proportion coefficient less than a preset area proportion coefficient.

In this embodiment, stains in the section information graph can be eliminated respectively according to the area, the length and width, and the area proportionality coefficient of the connected domain. It should be noted that the determination of the above three rules will not be affected by the order of execution, the three rules can be executed simultaneously, and stains in the section information graph can be eliminated in any order that can be executed. Moreover, those skilled in the art can predict the effect of the above three rule determination on eliminating the stains in the section information graph without consideration of the order of execution in the first elimination module B53.

Specifically, as described herein:

the reason why adopts the judgment rule of eliminating the connected domain having an area less than a preset area is that the area of dust in the impurity and the spot-like stain on the section is at a few hundred pixel level, much less than the area of the tissue, thus, a connected domain with an area less than a preset area can be eliminated, and the preset area can be set to be similar to the area of general impurity, for example, 1200 pixels.

With respect to executing the judgment rule of eliminating the connected domain having a length-to-width ratio less than a preset length-to-width coefficient, for example, the step of eliminating the connected domain having a length-width ratio less than ⅕ or greater than 5, it is a connected domain wherein the connected domain having a special length-width ratio is deleted. Due to staining of section or other operational reasons, stains on the edges of cover slip tend to be in the form of horizontal strips or vertical strips and have a length and width, with very large size or very small size. Therefore, the connected domain with the special length-width ratio can be eliminated.

In the judgment rule of eliminating the connected domain having an area proportion coefficient less than a preset area proportion coefficient, divide the area of the connected domain by the product of the length and width of the area to obtain the area proportion coefficient. When the area proportion coefficient is less than a preset area proportion coefficient, for example ⅙, it indicates the contour of the connected domain is large, but that a little section information exists, because it is a domain composed by the connection of a plurality of long strip stains on the edges of the cover slip, therefore, the connected domain should be eliminated.

In this embodiment, the first elimination module B53 can be implemented by using a processor having image recognition and comparison function, which will not be repeated herein.

Figure 11:
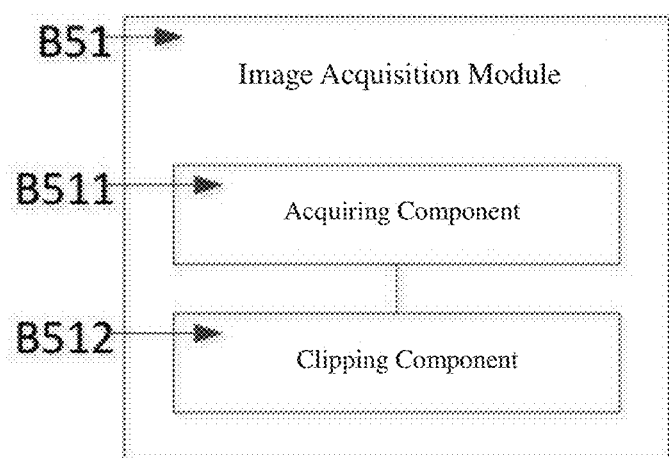
FIG. 11 is a schematic diagram of a specific structure of an image acquisition module on the basis of FIG. 7 in a preferred embodiment of the present invention.

In a preferred embodiment of the present invention, as shown in FIG. 11, wherein the image acquisition module B51 comprises:

an acquiring component B511, for acquiring a background image of the blank section image and the preview respectively;

a clipping component B512, connected to the acquiring component B511, for cutting off the edges of the background image and the preview respectively.

Specifically, in this embodiment, the pathological section is placed on a slide, and is covered with a cover slip, on the one hand, to prevent dust from falling onto the tissue, and on the other hand, to fix the tissue. The edges of the background image and the preview are the edges of the slide and the cover slip, and tissue information does not exist here. In order to exclude interference as much as possible, these edges need to be cut.

In a preferred embodiment, before the stains in the section information graph are eliminated by the first elimination module B53, in order to highlight the difference between the section tissue and most of the impurities, the first elimination module B53 can be used to perform image binarization processing on the section information graph, followed by the elimination of stains. More specific embodiments of achieving image binarization processing are known in the prior art, which will not be repeated herein.

Further, in this embodiment, in order to better distinguish the section tissue from the most impurities, to identify the section tissue, a threshold value on which the image binarization processing is based can be set to be slightly lower, so as to meet the identification requirements.

Further, in a preferred embodiment of the present invention, after the image binarization processing is performed on the section information graph, the first elimination module B53 can be used to perform an opening operation on the section information graph to separate the edge between the smaller connected domain and the larger connected domain to smooth the contour of the section information graph.

In a preferred embodiment of the present invention, the working principle of the identification unit B5 in the technical scheme of the present invention is illustrated by using FIGS. 12-20 as an example.

Figure 12:
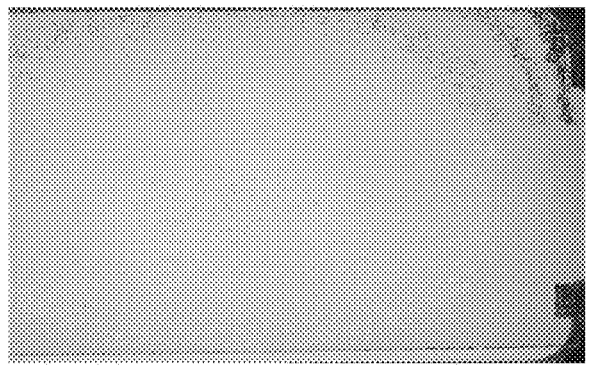
FIGS. 12-20 are schematic diagrams of the identification of the section tissue in a preferred embodiment of the present invention.
Figure 13:
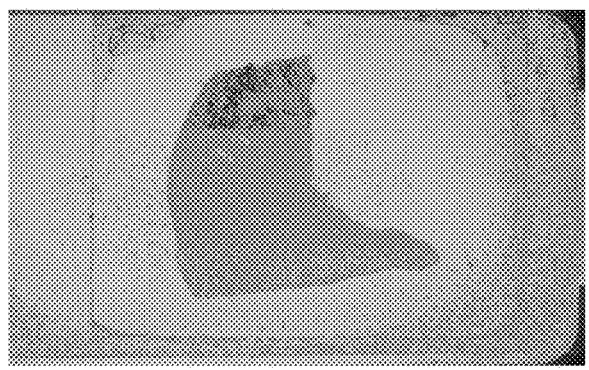
Figure 14:
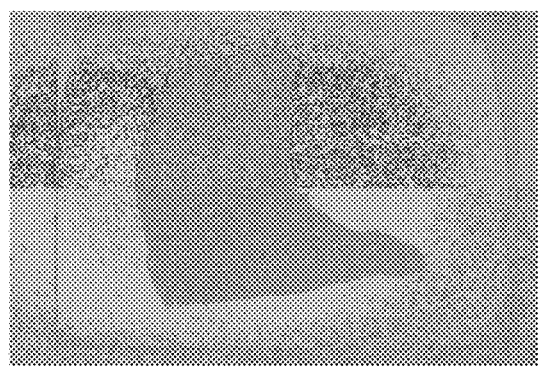
Figure 15:
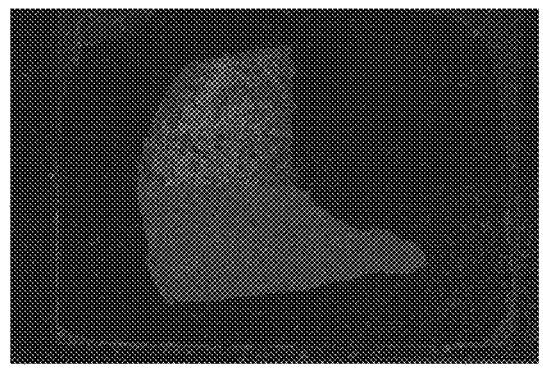
Figure 16:
Figure 17:
Figure 18:
Figure 19:
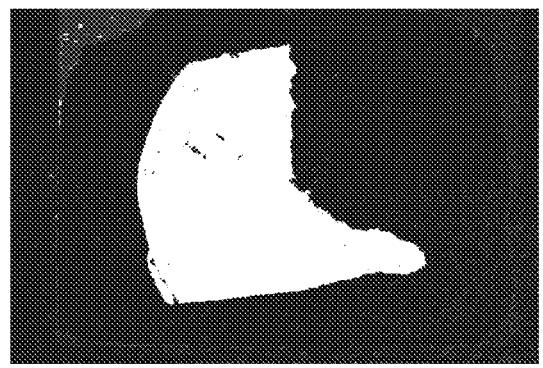
Figure 20:
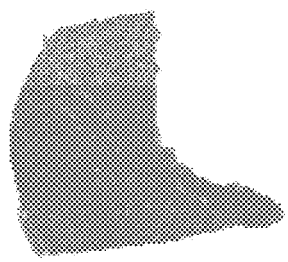

FIGS. 12-20 show the whole process of identifying the preview of the pathological section by using the identification unit B5 and finally obtaining the section tissue image in the technical scheme of the present invention. FIG. 12 shows a background image of a blank section, and FIG. 13 is a preview with tissues which is photographed. Since instruments are likely to be photographed within the edges of the background image and the preview, the edges of FIG. 12 and/or FIG. 13 may be cut off such that interference from the edges of the preview and/or the background image may be eliminated. FIG. 14 shows an embodiment of cutting off the edge in FIG. 13. Then, the gray value of the preview having been cut off the edge is subtracted from the gray value of the background image having been cut off the edge to obtain a section information graph as shown in FIG. 15. On the basis of FIG. 15, the image binarization processing is performed to further distinguish the tissue from the impurity, and FIG. 16 is obtained. Next, perform an opening operation on the image shown in FIG. 16 to remove tiny impurities, and therefore FIG. 17 is obtained. Further, the tissue section image shown in FIG. 18 can be obtained by performing the rule of geometric shape judgment (the first rule applied by the second elimination module B54); the tissue section image shown in FIG. 19 can also be obtained by the color judgment rule (the second rule applied by the second elimination module B54); and based on FIGS. 18 and 19, it is determined whether the connected domain is regarded as the tissue or not, and the identified result is shown in FIG. 20. In other words, in the embodiment, the second elimination module B54 applies two judgment rules of the connected domain at the same time, and only the connected domain that satisfies both of the two judgment rules can be regarded as the connected domain in which the section tissue exits.

Figure 21:
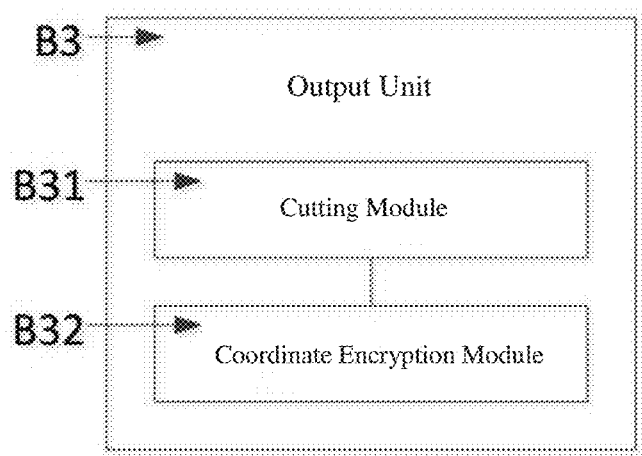
FIG. 21 is a schematic diagram of a specific structure of an output unit on the basis of FIG. 1 in a preferred embodiment of the present invention.

In a preferred embodiment of the present invention, as shown in FIG. 21, wherein the output unit B3 specifically comprises:

a cutting module B31, for cutting the digital pathological section image into a plurality of local images;

a coordinate encryption module B32, connected to the cutting module B31, for respectively performing an encryption operation on the coordinate information of each of the local images to obtain an encrypted information of each of the local images;

wherein, the output unit B3 sends the local images and the corresponding encrypted information to the remote server C, so as to send the digital pathological section image to the remote server C;

wherein, after the second client end E accesses the remote server C and obtains the stored local images and the corresponding encryption information associated to the digital pathological section image, each of the encrypted information is parsed to obtain the corresponding coordinate information, and according to the coordinate information, the local images are jointed together in sequence to form a completed digital pathological section image and the completed digital pathological section image is displayed, so that a user of the second client end E diagnoses the digital pathological section image.

Specifically, the current digital pathological section image is basically not encrypted or any common data encryption operations are barely performed in the transmission process. Therefore, the current digital pathological section image in the transmission process is prone to cause the leak of information, thus, patient's information security cannot be guaranteed. And the data confidentiality is relatively poor. In this embodiment, many improvements have been done in terms of encrypted transmission for the above problems.

Specifically, in this embodiment, each of the digital pathological section images is respectively divided into a plurality of local images, and each of the local images corresponds to a unique piece of coordinate information, and the plurality of local images form a global graph corresponding to the digital pathological section images.

After the digital pathological section image is encrypted, it is uploaded to the remote server C and managed by the remote server C. When the physician (the second client end E) needs to browse the digital pathological section image through the client end, the digital pathological section image need to be decrypted. If the digital pathological section image is leaked to the extranet, other client ends cannot access the encrypted information corresponding to the related digital pathological section image except for the remote server C responsible for managing the digital pathological section image. Therefore, the digital pathological section image will not be opened, and patient's information security can be ensured.

Moreover, the global graph of the digital pathological section image is divided into a plurality of local images, and the coordinate information of each local image is respectively encrypted to complete the encryption operation for the digital pathological section image, so as to avoid lowering the speed of browsing the encrypted digital pathological section image due to the excessively large size of the digital pathological section image. When the physician decrypts the digital pathological section image by using the second client end E, the plurality of local images are respectively decrypted to ensure the browsing speed and improve the user experience.

Therefore, in this embodiment, apart from the function of achieving the transmission of the digital pathological section image, the output unit B3 further comprises the function of dividing the digital pathological section image and respectively encrypting the local images. The output unit B3 may be a processing chip including data communication function, that is, a communication chip and a processor achieving data encryption function are integrated in a processing chip to achieve the functions of the output unit B3.

In conclusion, in the technical scheme of the present invention, the principle of encrypting and transmitting the digital pathological section image by output unit B3 specifically comprises:

first, a pathological section is scanned by the scanning end A to obtain an original pathological section image, and the original pathological section image is processed to form a digital pathological section image that can be transmitted to the remote server C;

then, in the output unit B3, the digital pathological section image is cut by the cutting module B31 to obtain a plurality of local images and the coordinate information of each of the local images corresponding to the global graph of the digital pathological section image, and a coordinate encryption module B32 is used to respectively perform an encryption operation on the coordinate information of each of the local images to obtain the encrypted information of each of the local images;

finally, the local images and the corresponding encrypted information are transmitted to the remote server C by the output unit B3, comprising;

when needing to browse the digital pathological section image, the physician may use the second client end E to retrieve all the local images and the encrypted information corresponding to the digital pathological section image to be browsed from the remote server C, and the encrypted information is decrypted to obtain the coordinate information corresponding to each of the local images. Then, the second client end E performs jointing operation on the local images upon the corresponding positions according to all the coordinate information, so as to obtain a complete digital pathological section image, and the completed digital pathological section image is provided to the physician for browsing.

In a preferred embodiment of the present invention, wherein the digital pathological section scanning system comprises a plurality of scanning ends A, each of the scanning ends A corresponding to one of the image processing ends B (FIG. 1 only shows one scanning end A);

each of the image processing ends has a unique authorization code, and each of the scanning ends has a unique machine code, and the authorization code and the machine code forms a key;

and the key is provided to the output unit of the image processing end for performing an encryption operation on the digital pathological section image, and the image processing end provides the key to the remote server while sending the digital pathological section image to the remote server.

Specifically, in this embodiment, the digital pathological section scanning system may comprise a plurality of scanner devices (the scanning end A), each of the scanner devices is connected to a specific image processing server (the image processing end B). The original pathological section image obtained by scanning via a specific scanning end A is processed via its specific image processing end B to obtain a digital pathological section image, and the obtained digital pathological section image is uploaded to the remote server C. Therefore, it can be considered that a scanning end A, together with its corresponding image processing end B in the digital pathological section scanning system, forms a workstation for obtaining the digital pathological section image by scanning.

In this embodiment, each of the scanning ends A has a unique machine code, and each of the image processing ends B also has a unique authorization code. The original pathological section image obtained by scanning via a specific scanning end A is processed via its specific image processing end B to obtain a digital pathological section image, and the key corresponding to the digital pathological section image is the key formed of the machine code of the scanning end A and the authorization code of the image processing end B. Thus, it can be ensured that the keys of the digital pathological section images output from different scanning ends A and their corresponding image processing ends B are different, in other words, it is possible to show which workstation the digital pathological section image comes from by means of the key.

Figure 22:
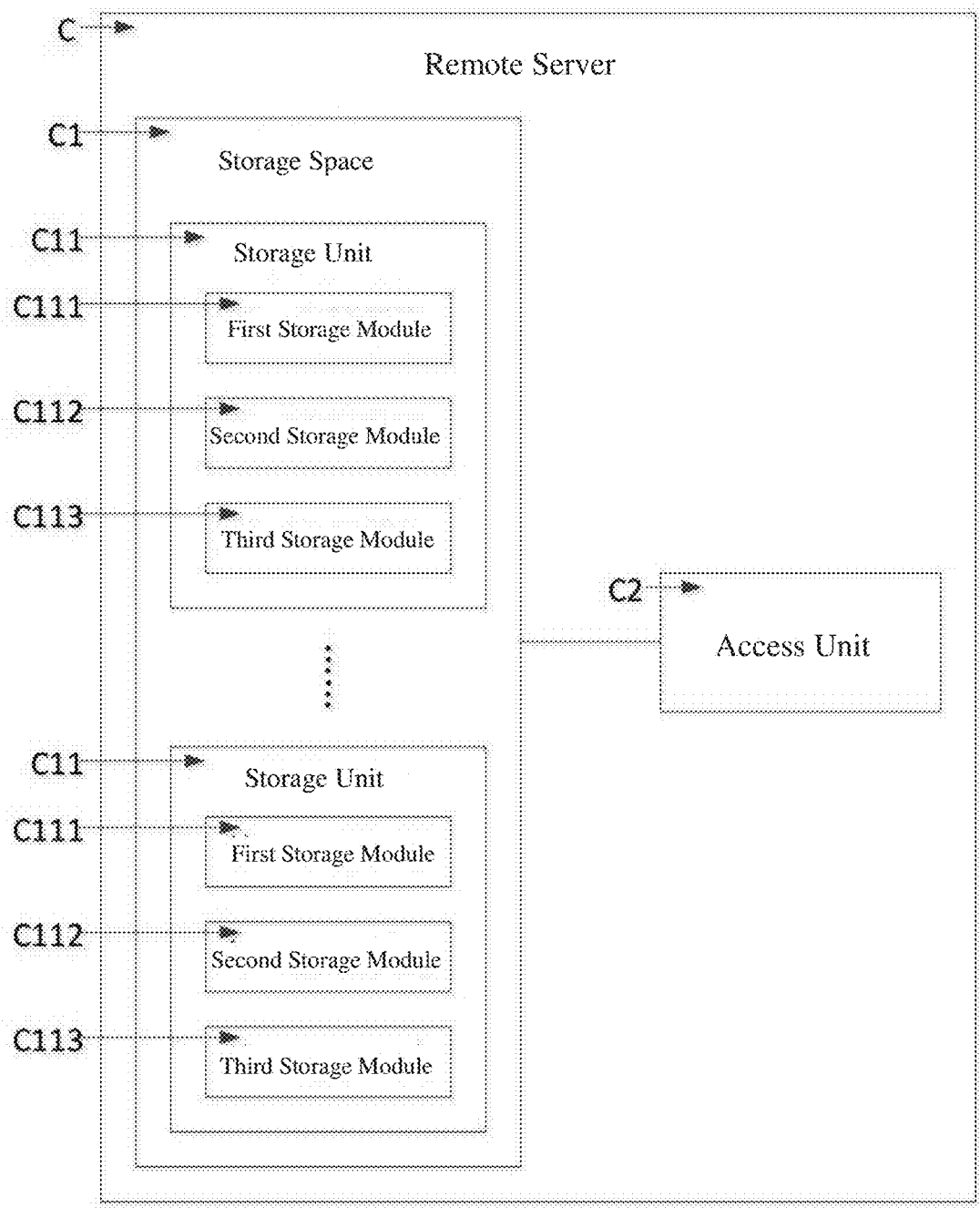
FIG. 22 is a schematic diagram of a specific structure of each storage unit in a remote server on the basis of FIG. 1 in a preferred embodiment of the present invention.

In a preferred embodiment of the present invention, as shown in FIG. 22, wherein each of the storage units C11 in the remote server C specifically comprises:

a first storage module C111, for storing the local images in the digital pathological section image;

a second storage module C112, for storing the encrypted information corresponding to each of the local images;

a third storage module C113, for storing the key corresponding to the digital pathological section image;

then as shown in FIG. 22, wherein, the remote server C further comprises:

an access unit C2, connected to the storage space C1, for obtaining, upon the access request of the second client end, the local images, the encryption information and the key from the storage unit C11, and the obtained local images, the encryption information and the key are sent to the second client end E.

Specifically, in this embodiment, the local images of the digital pathological section image only accessible to the attending physician associated with the storage unit C11 is stored in each of the storage units C11, however, in addition to the above local images, the encrypted information of each of the local images and the key of the digital pathological section image should also be stored in each of the storage units C11. When the second client end E accesses the digital pathological section image, the remoter server C provides an access unit C2 capable of sending the local images, the encrypted information and the key in the storage unit C11 to the second client end E for decryption.

In other embodiments of the present invention, if the second client end E chooses to browse the digital pathological section image online, the remote server C may also exhibit the function of online encryption, that is, the local images, performing encryption and jointing operation at the remote server C directly through the encrypted information and the key saved in the corresponding storage unit C11, then a complete digital pathological section image is provided to the attending physician.

Figure 23:
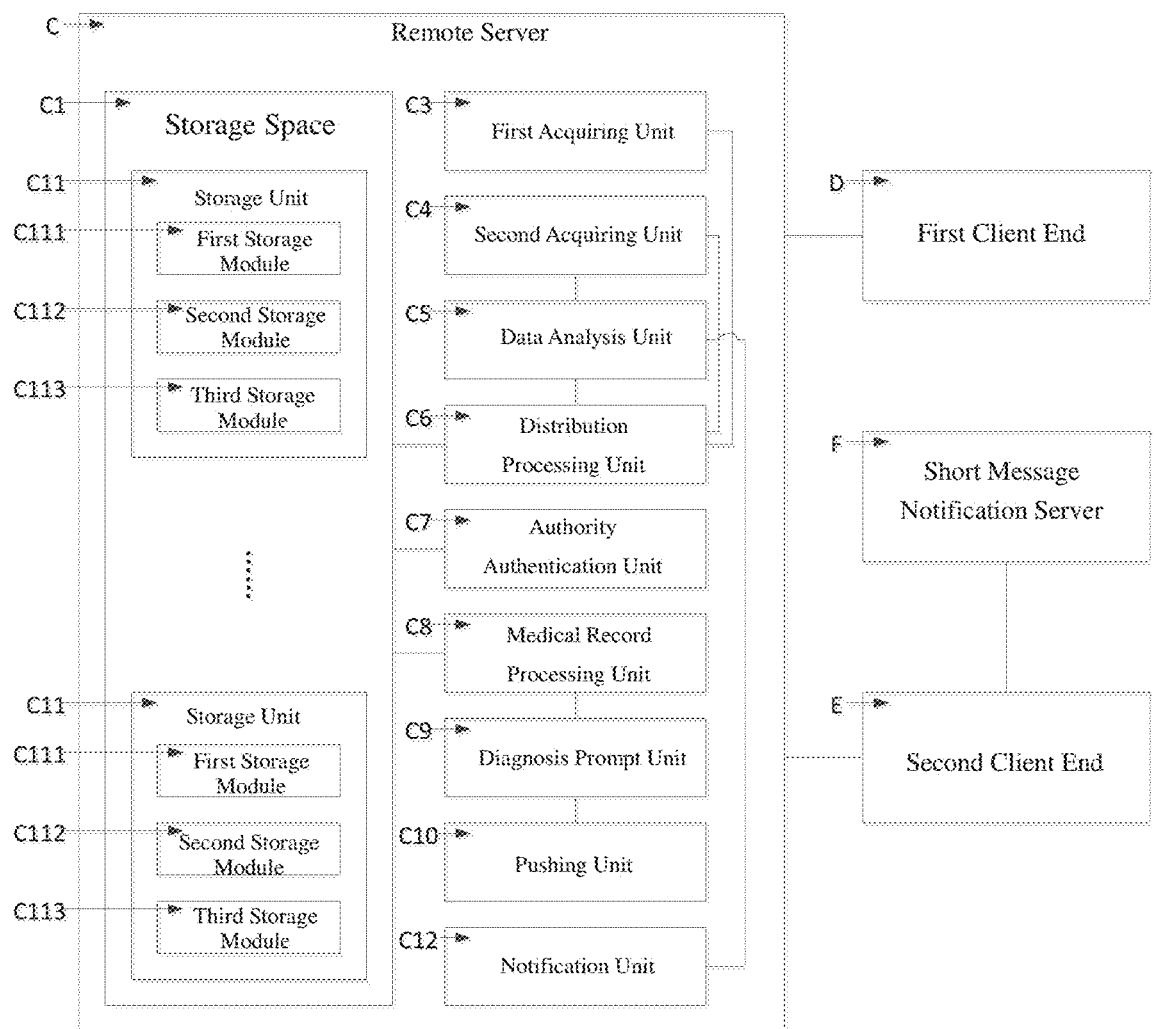
FIG. 23 is a schematic diagram of a specific structure of a remote server on the basis of FIG. 1 in a preferred embodiment of the present invention.

In a preferred embodiment of the present invention, as shown in FIG. 23, wherein the remote server C specifically comprises:

a first acquiring unit C3, for acquiring the digital pathological section image sent by the image processing end;

a second acquiring unit C4, for acquiring the medical record information sent by the first client end;

a data analysis unit C5, connected to the second acquiring unit C4, for acquiring the attending physician information by analyzing the medical record information;

a distribution processing unit C6, connected to the data analysis unit C5, the first acquiring unit C3, the second acquiring unit C4 and the storage space C1, respectively, for storing, according to the analyzed attending physician information, the corresponding medical record information and the digital pathological section image in the corresponding storage unit C11 in the storage space, and in the storage unit C11, the digital pathological section image and the medical record information are saved in association with one another;

an authority authentication unit C7, connected to the storage space C1, for verifying the account information and the password of the attending physician account provided by the second client end E;

and authorizing the second client end E permission to access the medical record information and the digital pathological section image in the corresponding storage unit C11 after the verification is passed; and a medical record processing unit C8, connected to the storage space C1, for diagnosing the digital pathological section image by the second client end E by remote login to form a diagnostic report corresponding to the digital pathological section image, and the diagnostic report is saved in the storage unit C11 in the storage space C1 corresponding to the digital pathological section image.

Specifically, in this embodiment, given the problem that an illness cannot be diagnosed timely since current attending physician is on a business trip or participating in an activity, the present invention manages to associate the digital pathological section image obtained outside of a hospital with the selected attending physician by means of the first client end D and the scanning end A, and the medical record information of the patient is sent to the remote server C for designating the specific attending physician to browse and diagnose the digital pathological section image of the patient.

The remote server C allocates a storage unit C11 to each attending physician. After the medical record information and the corresponding digital pathological section image sent by the first client end D is analyzed by the data analysis unit C4 in the remote server C to obtain the attending physician information thereof, the medical record information and the corresponding digital pathological section image are stored in the storage unit C11 of corresponding attending physician, and thus making it easier for the attending physician at the second client end E to check how many digital pathological section images there are in the storage unit C11 when logging in the remote server C, facilitating the attending physician to make a diagnosis timely.

When the diagnosis of the digital pathological section image of the patient needs to be made, the attending physician logs into the remote server C by entering account information and a password in the second client end E, and the remote server C identifies the account information and the password, if the account information and the password matches with the attending physician, the second client end E is authorized to access the corresponding storage unit C11 in the storage space C. Specifically, the remote server C may send the access path of the corresponding storage unit C11 to the second client end E, the second client end E then can browse and diagnose the digital pathological section image saved in the corresponding storage unit C11 according to the access path.

In this embodiment, the diagnosis made by the attending physician at the second client end E is processed by the medical record processing unit C7 in the remote server C to form a diagnostic report, and the diagnostic report is saved in the remote server C, wherein the remote server E may further send the diagnostic report to the corresponding first client end D, such that the patient involved may get to know the diagnostic result.

In this embodiment, the second client end E may access the medical record information and the corresponding digital pathological section image concerning the related patient in the remote server C by means of data access interface provided by the remote server C, and thus the attending physician at the second client end E may make a diagnosis in time.

In a preferred embodiment of the present invention, still as shown in FIG. 23, wherein the remote server further comprises:

a diagnosis prompt unit C9, connected to the medical record processing unit C8, for forming a diagnostic prompt information corresponding to the medical record information according to the generated diagnostic report; and a pushing unit C10, connected to the diagnosis prompt unit C9, for sending the diagnosis prompt information to the first client end D outputting the medical record information.

Specifically, in this embodiment, after the attending physician at the second client end E has made the diagnosis, the diagnosis prompt unit C9 will generate the diagnosis prompt message corresponding to the patient's medical record information, wherein the diagnosis prompt message indicates that the attending physician has made the diagnosis. At this point, the diagnosis prompt message is pushed to the corresponding first client end D by the pushing unit C10, and the first client end D may obtain the diagnostic report of related patient according to the diagnosis prompt message.

In a preferred embodiment of the present invention, as shown in FIGS. 1 and 23, the digital pathological section scanning system further comprises a short message notification server F, wherein the short message notification server F provides an interface for connecting to the remote server C, and the short message notification server F further remotely connects to the second client end E;

as shown in FIG. 23, the remote server C further comprises:

a notification unit C12, connected to the data analysis unit C4, for generating corresponding consultation prompt information according to the analyzed attending physician information;

wherein, invoke the interface via the remote server E to control the short message notification server F to send the consultation prompt information to the second client end E corresponding to the attending physician information.

Specifically, in this embodiment, in order to remind the attending physician to make contact with the patient for diagnosis, the remote server E generates the consultation prompt information through the notification unit C12, and the consultation prompt information is sent to second client end E of the corresponding attending physician by the short message notification server F via invoking the interface, then it is convenient for the attending physician to view the digital pathological section image and make a diagnosis in time.

Figure 24:
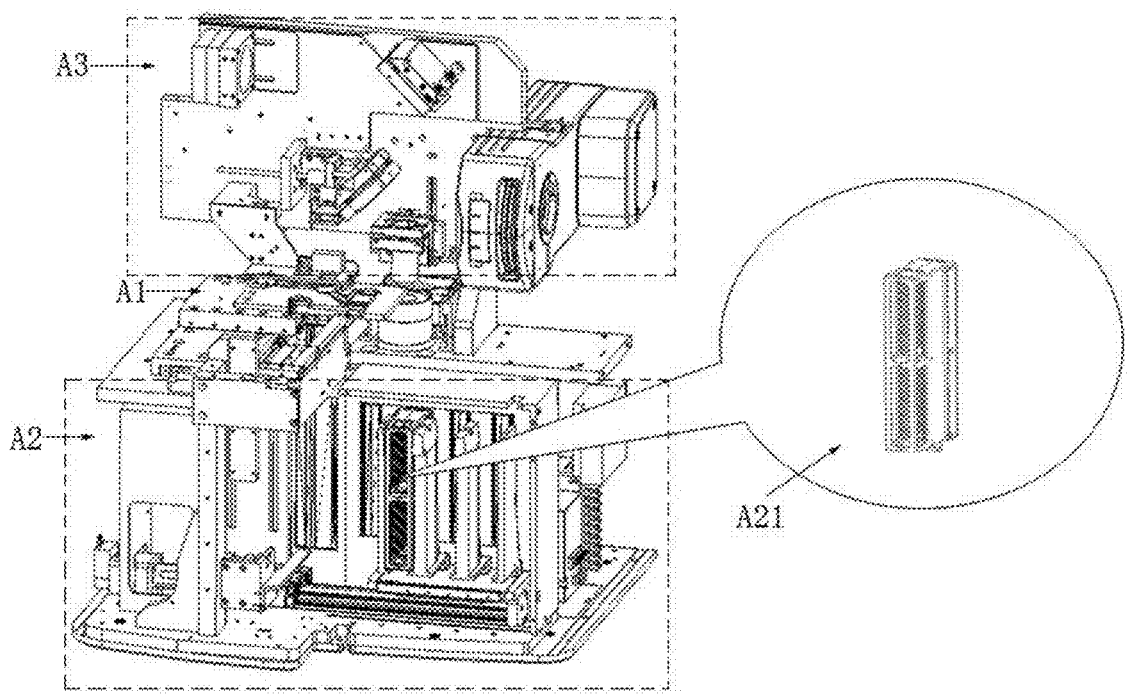
FIGS. 24-31 are schematic diagrams of the specific structure of the scanning end in the digital pathological section scanning system in a preferred embodiment of the present invention.

In a preferred embodiment of the present invention, as shown in FIG. 24, wherein the scanning end A further comprises:

a section platform A1 on which the pathological section to be scanned is placed for scanning by the scanning end A;

an automatic loading device A2, disposed below the section platform A1 and connected to the section platform A2, a plurality of the pathological sections to be scanned being placed in the automatic loading device A2, and the automatic loading device A2 lifts a pathological section to be scanned to the section platform at a time, for scanning by the scanning end A; and an illumination scanning device A3, disposed above the section platform A1, for scanning the pathological sections to be scanned placed on the section platform A1, to obtain the original pathological section image.

Specifically, in this embodiment, as shown in FIG. 24, the scanning end comprises a section platform A1 than can move on a horizontal XY plane, and the movement of the section platform A1 is controlled by a drive motor. An illumination scanning device A3 is disposed above the section platform A1 for providing light source required by the scanning end A, and for scanning the pathological section fixed on the slide on the section platform A1.

Figure 25:
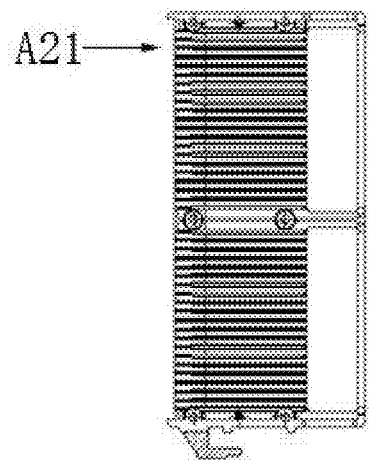
Figure 26:
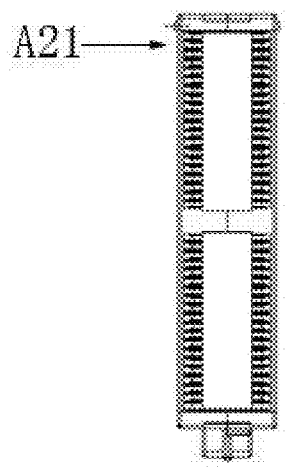

In a preferred embodiment of the present invention, the automatic loading device A2 comprises a section box A21 and a loader A22. A plurality of slides fixed with pathological sections are installed in the section box in advance, and each slide has a respective number. It is preferable that a section box A21 may disposably accommodate 40 slides, and the specific structure of the section box A21 is as shown in FIGS. 25-26.

Figure 27:
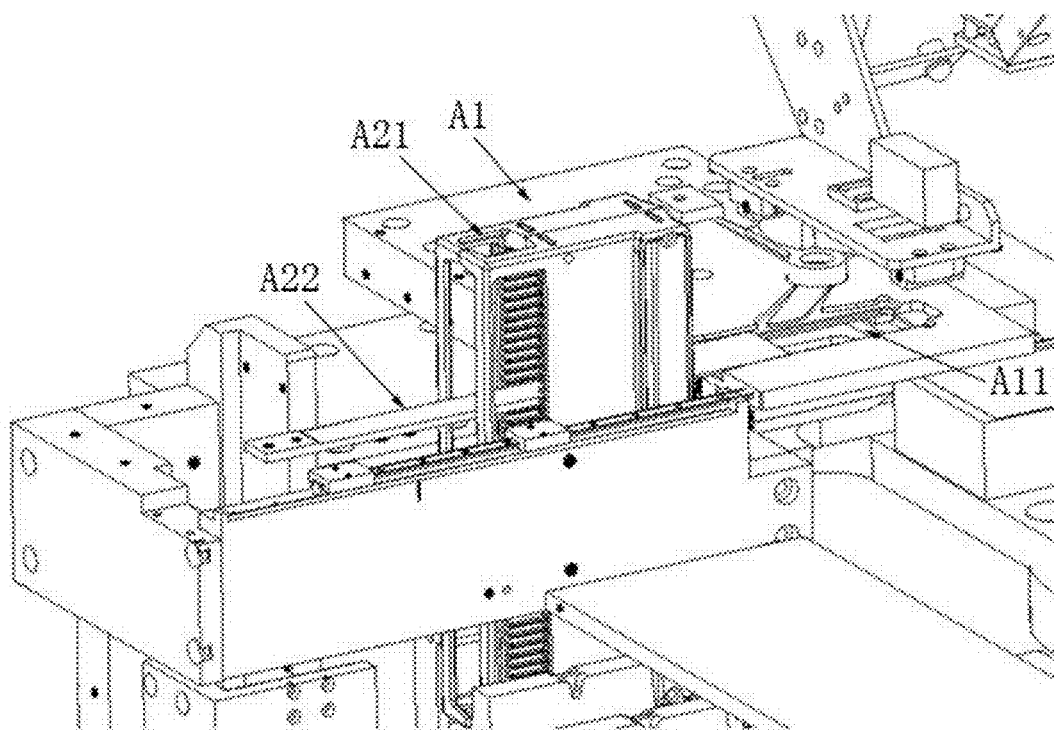
Figure 28:
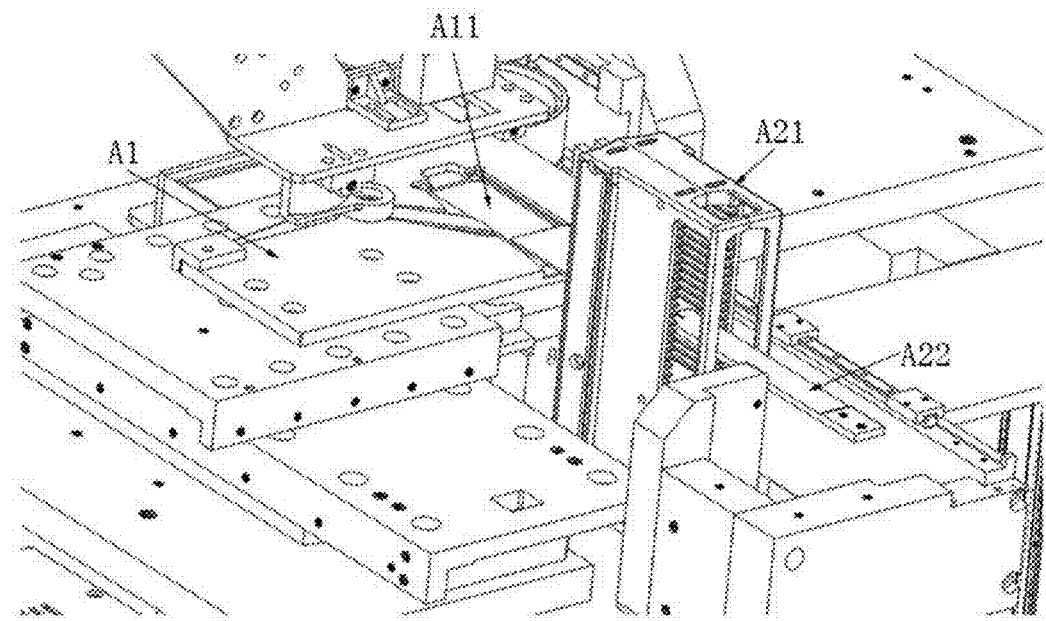

When a certain pathological section needs to be scanned, the driving circuit board in the automatic loading device A2 will load the slide with corresponding number in the section box A21 onto the section platform A1 located above the automatic loading device A2. Specifically, as shown in FIGS. 27 and 28, when a certain pathological section needs to be scanned, the automatic loading device A2 will rise to the position as high as the section platform A1, then the slide with corresponding number is pushed out of the section box A21 to the position A11 of the section box through the loader A22 (which is a pushing tongue shown in FIGS. 27 and 28) to be scanned by the scanning end A.

Other parts of the automatic loading device A2 are guide rail, lifting device and other auxiliary equipment, which will not be repeated herein.

Figure 29:
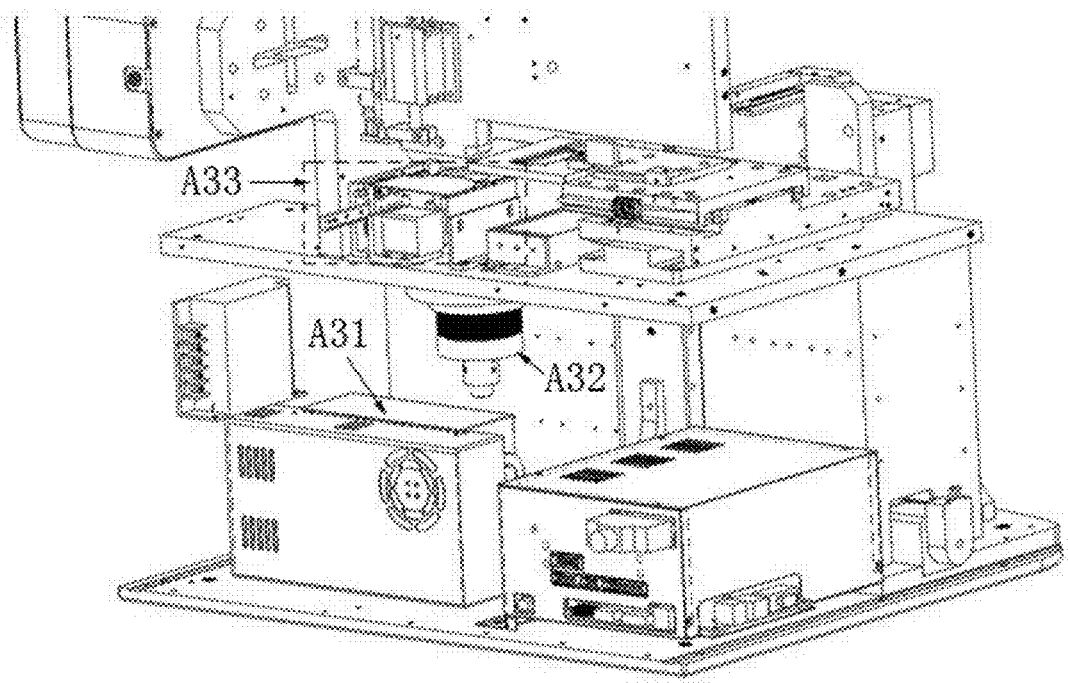
Figure 30:
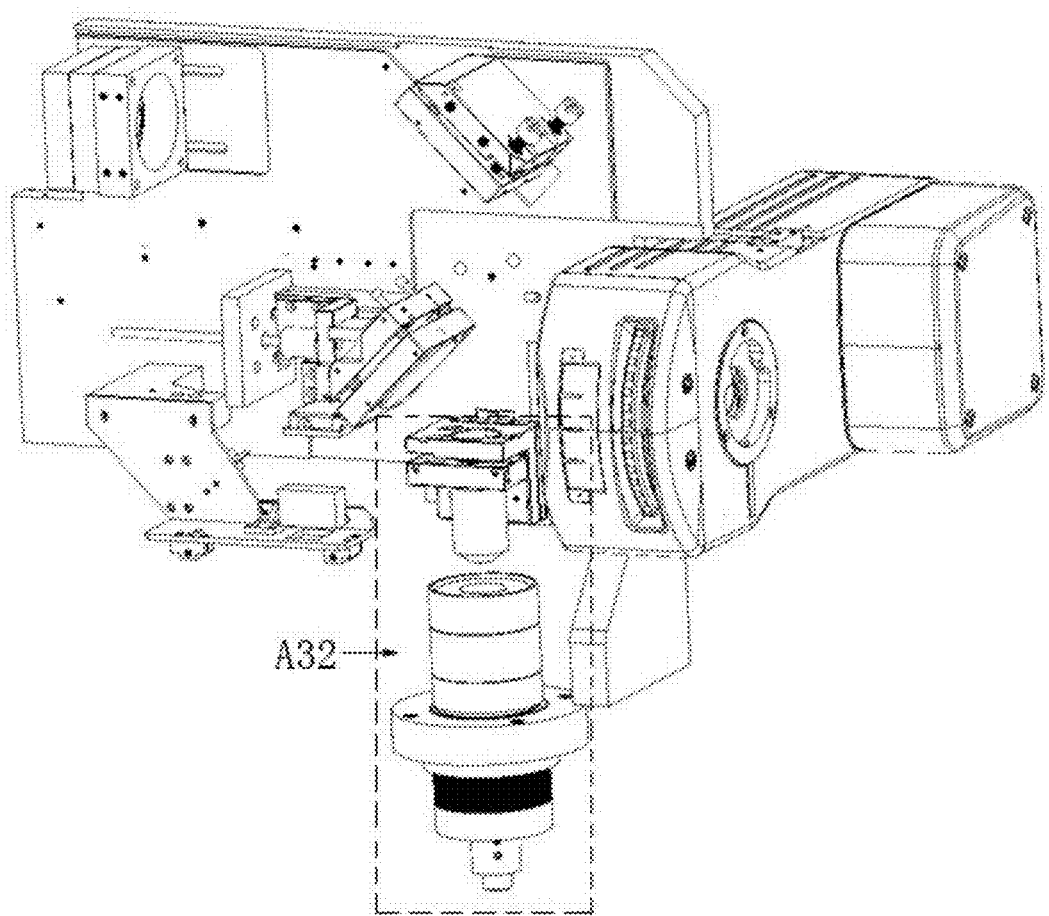
Figure 31:
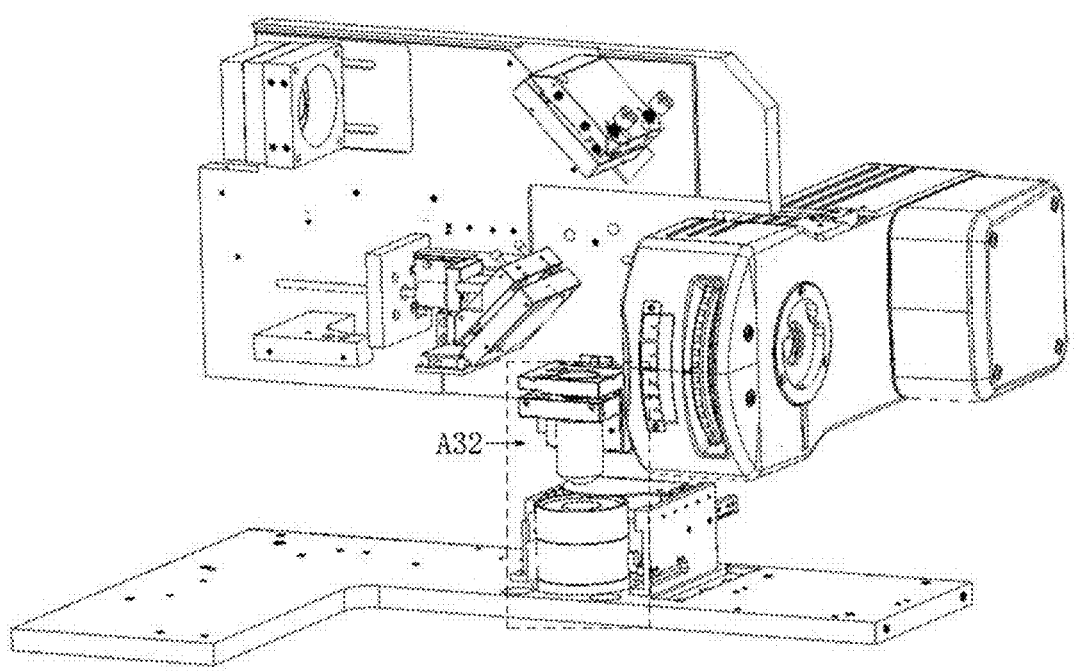

In a preferred embodiment of the present invention, as shown in FIGS. 29-31, wherein the illumination scanning device A3 further comprises:

a LED light source A31, for providing a light source required for scanning when the scanning end A scans the pathological section to be scanned;

a scanning unit A32, disposed at a side of the LED light source A31, for scanning the pathological section to be scanned; and a bright-to-fluorescence switching device A33, disposed on the scanning unit A32 and connected to the scanning unit A32, for controlling the scanning unit A32 to switch between a bright field scanning mode and a fluorescence scanning mode.

Specifically, in this embodiment, the portion shown in FIG. 29 is actually arranged on the back of the portion shown in FIG. 24. In FIG. 29, the LED light source A31 is arranged at one side of the scanning unit A32 and provides the light source necessary for scanning to the scanning unit A32. The scanning unit A32 may be a conventional scanning lens, comprising multiple objective lenses and a line camera having a scanning path similar to that of the scanning lens, which will not be repeated herein.

In this embodiment, the bright-to-fluorescence switching device A33 may make it possible for the scanning unit A32 to operate both at the bright field scanning mode and at the fluorescence scanning mode. The bright field scanning mode means scanning the pathological section by using the bright field transmission light; and the fluorescence scanning mode means scanning the pathological section by using fluorescence reflected light. In this embodiment, FIG. 30 shows a state in which the scanning unit A32 operates in the bright field scanning mode, and FIG. 31 shows a state in which the scanning unit A32 operates in the fluorescence scanning mode by shielding the lens via the bright-to-fluorescence switching device A33.

The foregoing is only the preferred embodiments of the invention, not thus limiting the embodiments and scope of the invention. Those skilled in the art should be able to realize that the schemes obtained from the content of specification and drawings of the invention are within the scope of the invention.

What is claimed is:

1. A digital pathological section scanning system, comprising:
    a scanning end, an image processing end, a remote server, a first client end and a second client end, wherein the scanning end is connected to the image processing end, and the remote server is connected to the image processing end, the first client end and the second client end respectively;
    wherein the scanning end is used for scanning a pathological section to be scanned to form an original pathological section image, and for transmitting the original pathological section image to the image processing end for processing;
    the image processing end is used for processing the original pathological section image transmitted by the scanning end to form a corresponding digital pathological section image and save the corresponding digital pathological section image, and for sending the digital pathological section image to the remote server;
    wherein the image processing end further comprises:
        a first detection unit for detecting a brightness value of the original pathological section image, and outputting a first detection result indicating whether the brightness value of the original pathological section image is qualified;
        a second detection unit for detecting a definition at jointing region of the original pathological section image formed by jointing a plurality of digital pathological section images, and for outputting a second detection result indicating whether the definition at the jointing region is qualified;
        an output unit, connected to the first detection unit and the second detection unit respectively, used for upon the first detection result and the second detection result, taking the original pathological section image having qualified brightness value and definition as the digital pathological section image, and sending the digital pathological section image to the remote server;
    wherein the first client end is used for transmitting a medical record information to the remote server, and the medical record information comprises an attending physician information representing an account of the attending physician which is selected by the first client end;
    the remote server comprises a storage space having a storage unit corresponding to the information of each of the attending physician;
    the remote server associates the obtained digital pathologic section image with the attending physician information included in the medical record information, and saves the digital pathological section image in the storage unit corresponding to the attending physician information; and
    the remote server simultaneously allows the second client end, that has verified login to the attending physician account, to access the digital pathological section saved in the storage unit corresponding to the attending physician account.

2. The digital pathological section scanning system of claim 1, wherein the first detection unit comprises:
    a first detection module for detecting a brightness value of the original pathological section image;
    a first standard module for providing a preset brightness range of a standard image corresponding to the original pathological section image; and
    a first comparison module, connected to the first detection module and the first standard module, respectively, for comparing the brightness value of the original pathological section image with the brightness range of the standard image;
    wherein when the brightness value of the original pathological section image is within the brightness range of the standard image, outputting the first detection result indicating that the brightness value of the original pathological section image is qualified; and
    wherein when the brightness value of the original pathological section image falls outside the brightness range of the standard image outputting the first detection result indicating that the brightness value of the original pathological section image is unqualified.

3. The digital pathological section scanning system of claim 2, wherein the first detection unit further comprises:
    an image compensation module, connected to the first comparison module, wherein, when the first comparison module outputs the first detection result indicating the brightness value of the original pathological section image is unqualified, the image compensation module outputs an illumination compensation instruction based on a difference between the brightness value of the unqualified original pathological section image and the brightness range of the standard image, then the image processing end feeds back the illumination compensation instruction to the scanning end to obtain the original pathological section image by controlling the scanning end to rescan.

4. The digital pathological section scanning system of claim 1, wherein the second detection unit comprises:
    a second detection module for processing the two digital pathological images that are jointed to each other, to obtain an image gradient of one digital pathological image to serve as a first gradient value, and to obtain an image gradient of the other digital pathological image to serve as a second gradient value;
    a second standard module for providing a preset gradient ratio in advance; and
    a second comparison module, connected to the second detection module and the second standard module, respectively, for comparing the ratio of the first gradient value to the second gradient value with the preset gradient ratio, and when the ratio is not matched with the preset gradient ratio, it is determined that the definition of the jointing region where the two digital pathological images are jointed to each other is unqualified, and thus outputting the second detection result indicating the definition of the jointing region where the original pathological images are jointed to each other is unqualified.

5. The digital pathological section scanning system of claim 4, wherein when the first gradient value is less than or equal to the second gradient value, the preset gradient ratio is less than or equal to 1;

then the second comparison module compares the ratio of the first gradient value to the second gradient value with the preset gradient ratio, and according to the comparison result, when the ratio of the first gradient value to the second gradient value is less than the preset gradient ratio, it is determined that the definition of the jointing region where the two digital pathological images are jointed to each other is unqualified; and when the ratio of the first gradient value to the second gradient value is greater than or equal to the preset gradient ratio, it is determined that the definition of the jointing region where the two digital pathological images are jointed to each other is qualified.

6. The digital pathological section scanning system of claim 5, wherein the second detection unit further comprises:

a storage module, connected to the second comparison module, for temporarily storing the digital pathological image whose definition is determined to be qualified by the second comparison module.

7. The digital pathological section scanning system of claim 4, wherein when the first gradient value is greater than the second gradient value, the preset gradient ratio is greater than 1;

then the second comparison module compares the ratio of the first gradient value to the second gradient value with the preset gradient ratio, and wherein according to the comparison result, when the ratio of the first gradient value to the second gradient value is greater than or equal to the preset gradient ratio, it is determined that the definition of the jointing region where the two digital pathological images are jointed to each other is unqualified; and when the ratio of the first gradient value to the second gradient value is less than the preset gradient ratio, it is determined that the definition of the jointing region where the two digital pathological images are jointed to each other is qualified.

8. The digital pathological section scanning system of claim 7, wherein the second detection unit further comprises:

a storage module, connected to the second comparison module, for temporarily storing the digital pathological image whose definition is determined to be qualified by the second comparison module.

9. The digital pathological section scanning system of claim 4, wherein the second detection unit further comprises:

an identification module, connected to the second comparison module, for identifying the jointing region on the digital pathological image where the second comparison module determines the definition of the digital pathological image is unqualified.

10. The digital pathological section scanning system of claim 1, wherein in the digital pathological section scanning system, section-cutting is performed on the human tissue of the same person, and two different original pathological section images are formed by scanning via the scanning end;

in the image processing end, the scanning system respectively detects the brightness value and the definition of the jointing region of the two original pathological section images, and forms two digital pathological section images respectively corresponding to the two original pathological section images, serving as a first section image and a second section image;

wherein the first section image is located in a first XOY coordinate axis which functions one endpoint of the first section image as an original point, and the second section image is located in a second XOY coordinate axis which functions one endpoint of the second section image as an original point; and the image processing end further comprises:

an adjusting unit, connected to the output unit, for adjusting, before the digital pathological section image is sent out by the output unit, the second section image according to the relative position between the first section image and the second section image, and integrating the second section image and the first section image into a corresponding digital pathological section image to be sent to the remote server by the output unit.

11. The digital pathological section scanning system of claim 10, wherein the adjusting unit comprises:

a background processing module for expanding the outline size of the first section image and filling the enlarged portion of the first section image with a blank background;

a first rotating module, connected to the background processing module, for aligning the endpoint in the second section image, coinciding with the original point of the second XOY coordinate axis, with a preset rotating point in the first section image;

a first grayscale processing module, connected to the first rotating module, for processing the first section image to obtain a gray value of a preset first determination point, and processing the second section image to obtain a gray value of a second determination point corresponding to the first determination point, followed by obtaining a gray comparison value under the current relative position between the first section image and the second section image;

a second rotating module, connected to the first rotating module, for rotating the second section image clockwise about the endpoint coinciding with the original point of the second XOY coordinate axis by a preset angle;

a determination module, connected to the first grayscale processing module and the second rotating module respectively, for determining, after the second rotating module rotates the second section image, whether the second section image has rotated about 360 degrees relative to an initial position, and outputting a determination result;

wherein the first grayscale processing module is further configured to perform, according to the determination result, the grayscale processing again when the second section image has not rotated about 360 degrees relative to the initial position; and the second rotating module is further configured to continue rotating, according to the determination result, the second section image when the second section image has not rotated about 360 degrees relative to the initial position; and an adjusting module, connected to the first grayscale processing module and the determination module respectively, for obtaining, according to the determination result, the gray value with the smallest value when the second section image has rotated about 360 degrees relative to the initial position, and adjusting the second section image according to the relative position between the first section image and the second section image corresponding to the obtained grayscale value.

12. The digital pathological section scanning system of claim 11, wherein the background processing module enlarges the first section image to an image with a width and a height of A, and fills the enlarged portion of the first section image with a blank background;
wherein $$A = \sqrt[2]{W_1^2 + H_1^2}$$

$W_1$ represents the width of the first section image; and
$H_1$ represents the height of the first section image.

13. The digital pathological section scanning system of claim 12, wherein the value range of the coordinate (m, n) of the preset rotating point satisfies the following:

$$0 \le m < W1-W2;$$

$$0 \le n < H1-H2;$$

wherein
m represents the X-axis coordinate of the preset rotating point in the first XOY coordinate axis;
n represents the Y-axis coordinate of the preset rotating point in the first XOY coordinate axis;
$W_1$ represents the width of the first section image;
$H_1$ represents the height of the first section image;
$W_2$ represents the width of the second section image; and
$H_2$ represents the height of the second section image.

14. The digital pathological section scanning system of claim 11, wherein the preset coordinate of the first determination point has a preset value range;
then the first grayscale processing module further comprises:
a first grayscale processing component for processing the first section image to obtain a gray value of each of the first determination point within the value range to serve as a first grayscale value;
a second grayscale processing component for processing the second section image to obtain a gray value of each of the second determination point corresponding to each of the first determination point within the value range to serve as a second grayscale value;
a third grayscale processing component, connected to the first grayscale processing component and the second grayscale processing component, respectively, for obtaining, according to the first gray value and the corresponding second grayscale value, each corresponding grayscale comparison value respectively; and
a grayscale acquisition component, connected to the third grayscale processing component, for obtaining the grayscale comparison value with the smallest value, serving as the grayscale comparison value under the current relative position between the first section image and the second section image.

15. The digital pathological section scanning system of claim 14, wherein the third grayscale processing component obtains the grayscale comparison value according to the following formula:

$$S(m,n) = \Sigma_{i=0,j=0}^{i=W2-1, j=H2-1} |P_1 - P_2|$$

wherein
S(m,n) represents the grayscale comparison value;
(m,n) represent the coordinate value of the preset rotating point, m is the X-axis coordinate of the preset rotating point in the first XOY coordinate axis, and n is the Y-axis coordinate of the preset rotating point in the first XOY coordinate axis;
(i, j) represent the coordinate value of the second determination point, i is the X-axis coordinate of the second determination point in the second XOY coordinate axis, and j is the Y-axis coordinate of the second determination point in the second XOY coordinate axis;
$W_2$ represents the width of the second section image;
$H_2$ represents the height of the second section image;
$P_1$ represents the first grayscale value; and
$P_2$ represents the second grayscale value.

16. The digital pathological section scanning system of claim 14, wherein the grayscale acquisition component obtains the grayscale comparison value with the smallest value, serving as the grayscale comparison value under the current relative position between the first section image and the second section image, and for recording the rotation angle of the second section image relative to the initial position; and
wherein the adjusting module rotates the second section image according to the rotation angle corresponding to the obtained grayscale comparison value with the smallest value.

17. The digital pathological section scanning system of claim 1, wherein a preview of the pathological section is obtained by pre-scanning before the scanning end scans the pathological section; and
the image processing end further comprises:
an identification unit, for recognizing the preview to obtain a section tissue image in the preview;
wherein the image processing end transmits the section tissue image back to the scanning end, and the scanning end scans the pathological section according to the section tissue image.

18. The digital pathological section scanning system of claim 17, wherein a blank section image is obtained by scanning via the scanning end in advance; and
the identification unit comprises:
an image acquisition module for obtaining a background image of the blank section image and the preview, respectively;
a second grayscale processing module, connected to the image acquisition module, for subtracting the gray value of the background image from the gray value of the preview to obtain a section information graph;
a first elimination module, connected to the second grayscale processing module, for performing traversal processing on the connected domains of the section information graph, and eliminating stains in the section information graph;
a second elimination module, connected to the first elimination module, for respectively judging, according to the attribute of the connected domain, whether each connected domain in the section information graph having been eliminated the stains is a section tissue, and eliminating the connected domain which is not the section tissue; and
a retention module, connected to the second elimination module, for retaining the section information graph as the section tissue image after the connected domain which does not belong to the section tissue is eliminated.

19. The digital pathological section scanning system of claim 18, wherein the image acquisition module comprises:

an acquiring component for acquiring a background image of the blank section image and the preview respectively; and a clipping component, connected to the acquiring component, for cutting off the edge portions of the background image and the preview respectively.

20. The digital pathological section scanning system of claim 1, wherein the output unit comprises:

a cutting module for cutting the digital pathological section image into a plurality of local images; and a coordinate encryption module, connected to the cutting module, for respectively performing an encryption operation on the coordinate information of each of the local images to obtain an encrypted information of each of the local images;

wherein, the output unit sends the local images and the corresponding encrypted information to the remote server, so as to send the digital pathological section image to the remote server; and wherein, after the second client end accesses the remote server and obtains the stored local images and the corresponding encryption information associated to the digital pathological section image, each of the encrypted information is parsed to obtain the corresponding coordinate information, and according to the coordinate information, the local images are jointed in sequence to form a completed digital pathological section image and the completed digital pathological section image is displayed, so that a user of the second client end diagnoses the digital pathological section image.

21. The digital pathological section scanning system of claim 20, wherein the digital pathological section scanning system comprises a plurality of scanning ends, each of the scanning ends corresponding to one of the image processing ends;

each of the image processing ends has a unique authorization code, and each of the scanning ends has a unique machine code, and the authorization code and the machine code form a key; and wherein the key is provided to the output unit of the image processing end for performing an encryption operation on the digital pathological section image, and the image processing end provides the key to the remote server while sending the digital pathological section image to the remote server.

22. The digital pathological section scanning system of claim 21, wherein each of the storage units in the remote server comprises:

a first storage module for storing the local images in the digital pathological section image;

a second storage module for storing the encrypted information corresponding to each of the local images; and a third storage module for storing the key corresponding to the digital pathological section image;

wherein, the remote server further comprises:

an access unit, connected to the storage space, for obtaining, upon the access request of the second client end, the local images, the encryption information and the key from the storage unit, and the obtained local images, the encryption information and the key are sent to the second client end.

23. The digital pathological section scanning system of claim 1, wherein the remote server comprises:

a first acquiring unit for acquiring the digital pathological section image sent by the image processing end;

a second acquiring unit for acquiring the medical record information sent by the first client end;

a data analysis unit, connected to the second acquiring unit, for acquiring the attending physician information by analyzing the medical record information;

a distribution processing unit, connected to the data analysis unit, the first acquiring unit, the second acquiring unit and the storage space, respectively, for storing, according to the analyzed attending physician information, the corresponding medical record information and the digital pathological section image in the corresponding storage unit in the storage space, and in the storage unit, the digital pathological section image and the medical record information are saved in association with each another;

an authority authentication unit, connected to the storage space, for verifying the account information and the password of the attending physician account provided by the second client end; and authorizing the second client end permission to access the medical record information and the digital pathological section image in the corresponding storage unit after the verification is passed; and a medical record processing unit, connected to the storage space, for diagnosing the digital pathological section image by the second client end by remote login to form a diagnostic report corresponding to the digital pathological section image, and the diagnostic report is saved in the storage unit in the storage space corresponding to the digital pathological section image.

24. The digital pathological section scanning system of claim 23, wherein the remote server further comprises:

a diagnosis prompt unit, connected to the medical record processing unit, for forming a diagnostic prompt information corresponding to the medical record information according to the generated diagnostic report; and a pushing unit, connected to the diagnosis prompt unit, for sending the diagnosis prompt information to the first client end outputting the medical record information.

25. The digital pathological section scanning system of claim 23, further comprising:

a short message notification server, wherein the short message notification server provides an interface for connecting to the remote server, and the short message notification server further remotely connects to the second client end; the remote server further comprises:

a notification unit, connected to the data analysis unit, for generating corresponding consultation prompt information according to the analyzed attending physician information;

wherein calling the interface via the remote server to control the short message notification server to send the consultation prompt information to the second client end corresponding to the attending physician information.

26. The digital pathological section scanning system of claim 1, wherein the scanning end further comprises:

a section platform on which the pathological section to be scanned is placed for scanning by the scanning end;

an automatic loading device, disposed below the section platform and connected to the section platform, a plurality of the pathological sections to be scanned being placed in the automatic loading device, and the automatic loading device lifts a pathological section to be scanned to the section platform at a time, for scanning by the scanning end; and an illumination scanning device, disposed above the section platform, for scanning the pathological sections to be scanned placed on the section platform, to obtain the original pathological section image.

27. The digital pathological section scanning system of claim 26, wherein the illumination scanning device further comprises:

an LED light source for providing a light source required for scanning when the scanning end scans the pathological section to be scanned;

a scanning means, disposed at a side of the LED light source, for scanning the pathological section to be scanned; and a bright-to-fluorescence switching device, disposed on the scanning means and connected to the scanning means, for controlling the scanning means to switch between a bright field scanning mode and a fluorescence scanning mode.

28. The digital pathological section scanning system of claim 26, wherein the automatic loading device comprises a section box and a loader;

wherein a plurality of slides comprising the pathological sections to be scanned are placed in the section box in advance, and each of the slides has a preset number; and wherein when the user selects the slide to be scanned according to the number, the loader pushes out the selected slide in the section box and places it in the section box of the section platform to be scanned by the illumination scanning device.

* * * * *